(12) United States Patent
Morard et al.

(10) Patent No.: US 12,307,674 B2
(45) Date of Patent: May 20, 2025

(54) LOW LATENCY INTERACTIVE SEGMENTATION OF MEDICAL IMAGES WITHIN A WEB-BASED DEPLOYMENT ARCHITECTURE

(71) Applicant: GE Precision Healthcare LLC, Milwaukee, WI (US)

(72) Inventors: Vincent Morard, Chassieu (FR); Jorge Hernandez Londono, Versailles (FR)

(73) Assignee: GE Precision Healthcare LLC, Waukesha, WI (US)

( * ) Notice: Subject to any disclaimer, the term of this patent is extended or adjusted under 35 U.S.C. 154(b) by 599 days.

(21) Appl. No.: 17/649,829

(22) Filed: Feb. 3, 2022

(65) Prior Publication Data

US 2023/0245317 A1 Aug. 3, 2023

(51) Int. Cl.
| | |
|---|---|
| *G06T 7/11* | (2017.01) |
| *G06N 3/08* | (2023.01) |
| *G16H 30/40* | (2018.01) |
| *H04L 67/12* | (2022.01) |

(52) U.S. Cl.
CPC ............... *G06T 7/11* (2017.01); *G06N 3/08* (2013.01); *G16H 30/40* (2018.01);
(Continued)

(58) Field of Classification Search
USPC ......... 128/897–899, 920–925; 382/128–134, 382/154–159, 173–180, 232–253;
(Continued)

(56) References Cited

U.S. PATENT DOCUMENTS

| | | | |
|---|---|---|---|
| 8,233,658 B2 * | 7/2012 | Beak | G06F 21/32 382/181 |
| 11,049,289 B2 | 6/2021 | Morard et al. | |

(Continued)

OTHER PUBLICATIONS

Rodrigo Benenson; Large-scale interactive object segmentation with human annotators; 2019 (Year: 2019).*

(Continued)

*Primary Examiner* — Marcellus J Augustin
(74) *Attorney, Agent, or Firm* — Amin, Turocy & Watson, LLP

(57) ABSTRACT

Techniques are described that facilitate interactive segmentation of medical images with low latency in a cloud-based medical imaging application. According to an embodiment, a system is provided that comprises a memory that stores computer executable components, and a processor that executes the computer executable components stored in the memory. The computer executable components comprise a reception component that receives a compressed representation of a three-dimensional (3D) medical image generated from the 3D medical image by an encoder network of a deep neural network model comprising an encoder network and a decoder network, an interaction component that receives user input relative to a displayed portion of the 3D medical image indicating an object included in the displayed portion for segmentation, and a segmentation component that generates a segmentation mask for the object based on the user input using the compressed representation and the decoder network.

20 Claims, 11 Drawing Sheets

(52) U.S. Cl.
CPC ...... *G06T 2200/04* (2013.01); *G06T 2200/24* (2013.01); *G06T 2207/20081* (2013.01); *G06T 2207/20084* (2013.01); *G06T 2207/20104* (2013.01); *G06T 2207/30004* (2013.01); *H04L 67/12* (2013.01)

(58) Field of Classification Search
USPC ........ 600/425–528, 921; 706/1–62, 900–903
See application file for complete search history.

(56) References Cited

U.S. PATENT DOCUMENTS

| | | | |
|---|---|---|---|
| 2009/0136096 A1 | 5/2009 | Sirohey et al. | |
| 2022/0108685 A1* | 4/2022 | Petrov | G06N 3/044 |
| 2022/0391633 A1* | 12/2022 | Harikumar | G06V 10/82 |

OTHER PUBLICATIONS

Navis Alemi Koohbanani; NuClick: A Deep Learning Framework for Interactive Segmentation of Microscopy Images; 2020 (Year: 2020).*

K. Maninis; Deep Extreme Cuts: From Extreme point to Object Segmentation; 2018 (Year: 2018).*
Peng Yuqing; Unet Network-Based Lung Lobe Segmentation Method and Apparatus, Computer Readable Storage Medium; 2020 (Year: 2020).*
Koohbanani, N. A. et al. | "NuClick: A deep learning framework for interactive segmentation of microscopic images". arXiv:2005.14511v2 [cs.CV] Jul. 7, 2020, 16 pages.
Wang. G. et al. | "Interactive Medical Image Segmentation using Deep Learning with Image-specific Fine-tuning". arXiv:1710.04043v1 [cs.CV] Oct. 11, 2017, 11 pages.
Sakinis, T. et al. | "Interactive segmentation of medical images through fully convolutional neural networks". arXiv:1903.08205v1 [cs.CV] Mar. 19, 2019, 10 pages.
Liu, Z. et al. | "Machine Vision Guided 3D Medical Image Compression for Efficient Transmission and Accurate Segmentation in the Clouds". arXiv:1904.08487v1 [cs.CV] Apr. 9, 2019, 10 pages.
Maninis, K.-K. et al. | "Deep Extreme Cut: From Extreme Points to Object Segmentation". arXiv:1711.09081v2 [cs.CV] Mar. 27, 2018, 10 pages.
Benenson, R. et al. | "Large-scale interactive object segmentation with human annotators". arXiv:1903.10830v2 [cs.CV] Apr. 17, 2019, 10 pages.

* cited by examiner

LOW LATENCY INTERACTIVE SEGMENTATION OF MEDICAL IMAGES WITHIN A WEB-BASED DEPLOYMENT ARCHITECTURE

TECHNICAL FIELD

This application relates to web-based medical imaging systems and more particularly to web-based medical imaging systems that facilitate interactive segmentation of medical images with low latency.

BACKGROUND

Advancements in internet technologies such as Hyper Text Markup Language 5 (HTML5) and JavaScript technology have enabled creation of advanced and rich web-based medical image view applications that allow radiologists to easily access teleradiology systems and remotely view medical images. Compared with picture archiving and communication systems or other imaging workstations which require dedicated hardware and software, a web-based application can be run on almost all personal computers without the need for powerful equipment on the client side. In this infrastructure, medical image data and complex processing tasks are moved from user computers to the cloud-based server. Users then launch a browser to access the server that allows visualization of medical image directly via HTML. In this case, a radiologist can implement the cloud-based medical image analysis using a personal computer from any location.

Although these frontend/backend architectures bring more flexibility to scale up with the number of users, they are attributed to a number of constraints especially with respect to providing real-time, computationally extensive processing tasks, such as those related to real-time annotation tools. For example, when many users request some computationally extensive calculation in the backend, such as three-dimensional (3D) organ segmentation, slowdowns and high latency responses can be observed. Thus, there is a need to reduce the load of the backend servers and if possible, to avoid network communication to improve the latency for real-time applications.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments, systems, computer-implemented methods, apparatus and/or computer program products are described herein that facilitate interactive segmentation of medical images with low latency under a cloud-deployment architecture.

According to an embodiment, a system is provided that comprises a memory that stores computer executable components, and a processor that executes the computer executable components stored in the memory. The computer executable components comprise a reception component that receives a compressed representation of a 3D medical image generated from the 3D medical image by an encoder network of a deep neural network model comprising an encoder network and a decoder network, wherein the neural network model is tailored to a clinical task related to the three-dimensional medical image. The computer executable components further comprise an interaction component that receives user input relative to a displayed portion of the 3D medical image indicating an object included in the displayed portion for segmentation, and a segmentation component that generates a segmentation mask for the object based on the user input using the compressed representation and the decoder network. The user input comprises applied user mark-up data to the displayed portion of the 3D image. The type of the applied user mark-up data can vary and may include but is not limited to: one or more points inside the object, one or more points outside the object, one or more points or lines indicating a boundary of the object, free-hand lines or shapes on or around the object, guided lines or shapes on or around the object.

In one or more embodiments, the system is deployed at a client device and the reception component receives the compressed representation from a server device via a network. (i.e., a web-based or cloud-based deployment architecture). With these embodiments, the server device executes the encoder network portion of the trained deep neural network model to generate the compressed representation of the 3D medical image and the segmentation weights for application by the decoder network which is deployed at the client device. The computer executable components can further comprise a preview component that renders the segmentation mask as overlay data over the object and the displayed portion of the 3D medical image. In various implementations, the interaction component can further receive additional user input relative to the displayed portion of the 3D medical image indicating the object included in the displayed portion for updated segmentation, wherein the segmentation component generates an updated segmentation mask for the object based on the new user input using the compressed representation and the decoder network, and wherein the preview component renders the updated segmentation mask as new overlay data over the object and the displayed portion of the 3D medical image. In this manner, the system provides for real-time interactive segmentation of the 3D medical image in which the user can repeatedly apply mark-ups to the displayed 3D medical image indicating an object or region of the object for segmentation and be presented with updated segmentation masks based on the mark-ups in real-time, wherein the computationally extensive 3D segmentation calculations are performed at the client side by the decoder network.

In various embodiments, the decoder network employs predetermined segmentation weights generated based on simulated user input data relative to training 3D medical images including the object, the simulated input indicating the object for segmenting as included in the training 3D medical images. The reception component can further receive the predetermined segmentation weights for application by the decoder network in association with reception of the compress representation. The deep neural network model comprises a previously trained model trained using the training 3D medical images as annotated with ground truth segmentation information for the object, wherein the training comprises generating the simulated user input data from the ground truth segmentation information. The training further comprises training the encoder network to generate compressed representations of the training 3D medical images and training the decoder network to generate segmentation masks for the object using based on the simulated user input data using the compressed representations. In some embodiments, the computer executable components further comprise a training component that performs the deep neural network model training for the clinical task.

In some embodiments, elements described in connection with the disclosed systems can be embodied in different forms such as a computer-implemented method, a computer program product, or another form.

DETAILED DESCRIPTION

Figure 1:
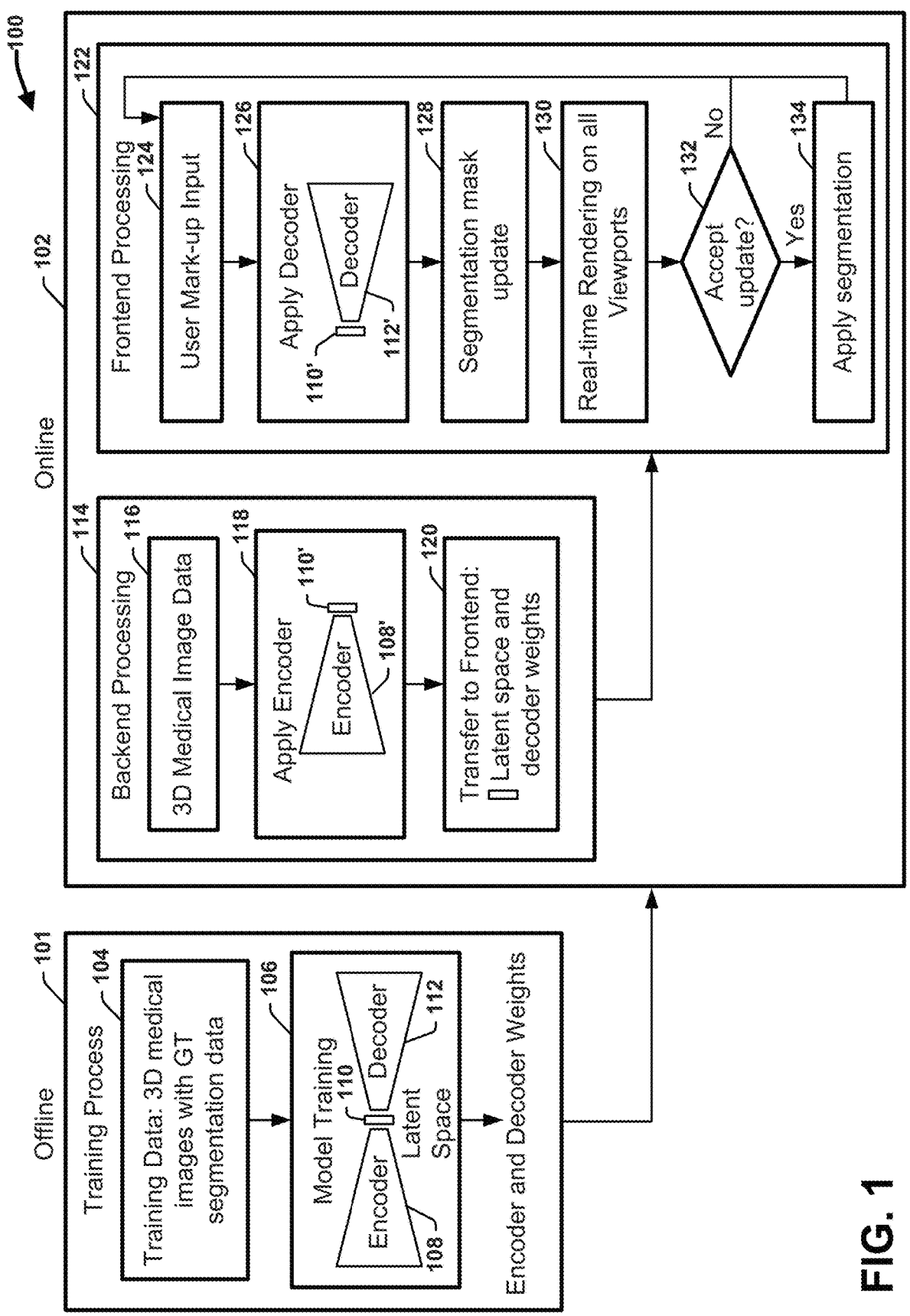
FIG. 1 illustrates a high-level flow diagram of an example computer implemented method that facilitates interactive segmentation of medical images with low latency under a cloud-deployment architecture in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to systems, computer-implemented methods, apparatus and/or computer program products that facilitate interactive segmentation of medical images with low latency under a cloud-deployment architecture. Medical image segmentation generally involves usage of computationally extensive segmentation models configured to generate segmentation masks over organs, regions or objects of interest depicted in a two-dimensional (2D) or three-dimensional (3D) medical images (e.g., volume representations of a scanned anatomical region of interest (ROI)). Some medical imaging applications employ these types of segmentation models to provide interactive segmentation based on applied user mark-ups to displayed 2D and/or 3D medical images indicating a desired object for segmentation. However, these medical imaging applications are generally deployed in a local deployment architecture in which all of the computationally extensive segmentation calculations are executed locally.

In a typical cloud-based or web-based medical imaging application, the computationally extensive processing tasks are moved to the backend servicers (i.e., server side) while the frontend services (i.e., the client side) provide the user facing interactive functions of the application accessed via a web-browser. For example, at the client side, the user interacts with the application graphical user interface (GUI) and the application sends a request to the backend each time an operation of associated with a displayed image is required, such as generation of a segmentation mask for a user marked portion of the displayed image. Although these frontend/backend architectures bring more flexibility to scale up with the number of users, they are attributed to a number of constraints especially with respect to providing real-time, computationally extensive processing tasks, such as those related to real-time annotation tools. For example, when many users request some computationally extensive calculation in the backend, such as 3D organ segmentation, slowdowns and high latency responses can be observed.

With this problem in mind, the disclosed subject matter provides techniques for interactive 3D medical image segmentation within a cloud-based medical imaging application while minimizing or eliminating latency complications attributed to conventional back-end processing tasks. To facilitate this end, the disclosed systems combine the power of deep learning methods for a high accuracy and repeatable processes with a smart calculation on the frontend that enable a real-time edition of the current segmentation. In particular, the disclosed techniques train a deep neural network model comprising an encoder network and a decoder network for a specific clinical segmentation task, such as a segmentation task tailored for a particular anatomical ROI (e.g., chest, abdomen, brain, etc.) and one or more objects for segmentation included in the anatomical ROI (e.g., a specific organ, a lesion, a diseased region, a vessel, scan prescription plane, etc.). The training data includes a large database of 3D medical images annotated with ground truth (GT) information corresponding to a 3D segmentation of the object as depicted in the respective training images. For example, the 3D medical images can include volumetric representations of the same or similar anatomical ROI (e.g., chest, abdomen, brain, etc.) generated from 3D medical scan data (e.g., magnetic resonance imaging (MRI) scan data, computed tomography (CT) scan data, or the like) captured for a plurality of different patients or subjects.

The model training processes involves training the encoder network to transform and compress the training 3D medical images into latent space representations that comprise a reduced set of the key features of the 3D medical images needed for performance of the specific clinical segmentation task. The latent space representations are then concatenated with simulated user inputs corresponding to different points within and around the segmented object. These points are generated from the GT 3D segmentation information and injected at each state of the decoder. The decoder network is further trained to generate estimated segmentation masks corresponding to the simulated user inputs from the latent space representations. The estimated segmentation masks are compared to the GT 3D segmentation information using a loss function (e.g., Dice loss or another loss function) and the model weights are determined/updated accordingly after many iterations of this training loop until convergence is reached.

After the encoder/decoder network model has completed training, the disclosed techniques separate the encoder network portion and the decoder network portion of the model for runtime 3D segmentation calculations under a web-based or cloud-based deployment architecture. In particular, the disclosed systems deploy the encoder network portion at the backend (i.e., server side) and the decoder network portion at the frontend (i.e., client side). At the tool initialization, the user can select a new 3D medical image for which the specific clinical segmentation task is applicable (e.g., corresponding to the training 3D medical images) for displaying and segmenting within the GUI of the imaging application. The backend server further performs the inference of the first part of the network: the encoder. This converts the 3D input medical image (or part of the 3D medical image) into a latent space representation: a small and compressed version of the 3D image using the encoder. The latent space representation and the corresponding decoder weights are further transferred to the frontend device (i.e., the client device). From now on, the frontend device has the required information to perform all the interactive edition of the segmentation mask. In this regard, each time the user moves the mouse/cursor (or the like) over the object to segment within a displayed portion of the 3D medical image, the decoder network generates a corresponding 3D segmentation mask from the latent space and the user inputs. For example, the user inputs may include applied marks on or over a displayed portion of the 3D medical image indicating the object or a region of the object for segmentation, such as lines, circles, inside/outside point markers, free-hand scribble and so on. The 3D segmentation mask is further rendered as an overlay over the displayed portion of the 3D medical image in the form of a preview image that the user can control in 3D. For each new mouse position, a new preview is shown to the user in real-time. As soon as the user click at a given position, the preview is accepted, and the segmentation is updated. This frontend process can be repeated several times until the user is satisfied with the segmentation.

The types of medical images processed/analyzed using the techniques described herein can include images captured using various types of image capture modalities. For example, the medical images can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MRI or simply MR) images, ultrasound (US) images, color flow doppler (CD) images, position emission tomography (PET) images, single-photon emissions computed tomography (SPECT) images, nuclear medicine (NM) images, and the like. The medical images can also include synthetic versions of native medical images such as synthetic X-ray (SXR) images, modified or enhanced versions of native medical images, augmented versions of native medical images, and the like generated using one or more image processing techniques.

A "capture modality" as used herein refers to the specific technical mode in which an image or image data is captured using one or more machines or devices. In this regard, as applied to medical imaging, different capture modalities can include but are not limited to: a 2D capture modality, a 3D capture modality, an RT capture modality, a XR capture modality, a DX capture modality, a XA capture modality, a PX capture modality a CT, a MG capture modality, a MR capture modality, a US capture modality, a CD capture modality, a PET capture modality, a SPECT capture modality, a NM capture modality, and the like.

As used herein, a "3D image" refers to digital image data representing an object, space, scene, and the like in three dimensions, which may or may not be displayed on an interface. 3D images described herein can include data representing positions, geometric shapes, curved surfaces, and the like. In an aspect, a computing device, such as a graphic processing unit (GPU) can generate a 3D image based on the data, performable/viewable content in three dimensions. For example, a 3D image can include a collection of points represented by 3D coordinates, such as points in a 3D Euclidean space (e.g., a point cloud). The collection of points can be associated with each other (e.g., connected) by geometric entities. For example, a mesh comprising a series of triangles, lines, curved surfaces (e.g. non-uniform rational basis splines ("NURBS")), quads, n-grams, or other geometric shapes can connect the collection of points. In an aspect, portions of the mesh can include image data describing texture, color, intensity, and the like.

A 3D medical image refers to a 3D or volumetric representation of an anatomical region of a patient. In some implementations, a 3D medical image can be captured in 3D directly by the acquisition device and protocol. In other implementations, a 3D medical image can comprise a reconstructed image that was generated from one-dimensional (1D) two-dimensional (2D) and/or 3D sensory and/or image data captured of the anatomical region of the patient. Some example 3D medical images include 3D volume images generated from CT scan data and MRI scan data, however the disclosed 3D medical images are not limited to these types of capture modalities. It is noted that the terms "3D image," "3D volume image," "volume image," "3D model," "3D object," "3D reconstruction," "3D representation," "3D rendering," and the like are employed interchangeably throughout, unless context warrants particular distinctions among the terms. It should be appreciated that such terms can refer to data representing an object, an anatomical region of the body, a space, a scene, and the like in three dimensions, which may or may not be displayed on an interface. The terms "3D data," and "3D image data" can refer to a 3D image itself, data utilized to generate a 3D image, data describing a 3D image, data describing perspectives or points of view of a 3D image, capture data (e.g., sensory data, images, etc.), meta-data associated with a 3D image, and the like. It is noted that the term "2D image" as used herein can refer to data representing an object, an anatomical region of the body, a space, a scene, and the like in two dimensions, which may or may not be displayed on an interface.

The terms "3D scan data," 3D exam data," and the like are used herein to refer to the collection of scan data acquired/generated in association with a performance of a 3D medical imaging scan, such as a CT scan, an MRI scan, a PET scan or the like. For example, 3D scan data can include 1D, 2D and 3D data that can be used to generate a 3D volumetric image of the scanned anatomy and to generate 2D scan images corresponding to slices of the 3D volumetric image from various perspective/orientations (e.g., relative to the axial plane, the coronal plane, the sagittal plane and other reformatted views). The term "scan slice," "image slice," "scan image," and the like are used herein interchangeably to refer to a reconstructed 2D image generated from 3D anatomy scan data that corresponds to a computer-generated cross-sectional image of an anatomical region of a patient.

The term "web platform" as used herein refers to any platform that enables delivery of content and services over a network (i.e., the web/Internet) using a network transfer protocol, such as hypertext transfer protocol (HTTP), HTML5, sFTP, or another network transfer protocol. For example, a web platform can include, but is not limited to, a web-application (i.e., an interactive website), a mobile website, a mobile application or the like. The terms "web platform," "web-based platform," "network platform," "platform," and the like are used herein. interchangeably unless context warrants particular distinction amongst the terms. The terms "web-based," and "cloud-based" are used herein interchangeable to refer to a system or application that employs a web platform to provide content and/or services (e.g., interactive 3D medical image segmentation) to end-users at a user device or client device.

The terms "algorithm" and "model" are used herein interchangeably unless context warrants particular distinction amongst the terms. The terms "artificial intelligence (AI) model" and "machine learning (ML) model" are used herein interchangeably unless context warrants particular distinction amongst the terms.

As used in this disclosure, the term "user," and the like refers to a person, entity, system, or combination thereof that interfaces with the subject 3D medical image segmentation system using a suitable computing device.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates a high-level flow diagram of an example computer implemented method 100 that facilitates interactive segmentation of medical images with low latency under a cloud-deployment architecture in accordance with one or more embodiments of the disclosed subject matter. Method 100 is composed of an offline process 101 and an online process 102. The offline process 101 corresponds to a machine learning model training process in which an 3D segmentation model is trained. The 3D segmentation model is a deep learning model comprising an encoder network (hereinafter encoder 108) and decoder network (hereinafter decoder 112), respectively employing convolutional neural network architecture. In accordance with the offline process 101 the 3D segmentation model is trained on a large database of training data 104 to perform interactive 3D segmentation for a specific clinical application. For example, the 3D segmentation model can be trained to perform 3D segmentation on 3D medical images depicting a specific anatomical ROI (e.g., brain, lungs, abdomen, or another anatomical ROI for which 3D imaging scans may be performed). In addition, relative to that specific anatomical ROI, the deep learning model may be tailored to perform segmentation of a specific object of interest, such as a specific organ, vessel, bone, soft tissue, lesion, diseased region and so on.

The training data 104 for training the 3D segmentation model will thus reflect the specific clinical application to which the deep learning model will be tailored. In various embodiments, the offline process 101 can involve training a plurality of different deep learning models to perform different types of 3D segmentations for different anatomical ROIs and/or different objects of interest within the different anatomical ROIs. Regardless of the specific anatomical ROI and object of interest for segmentation, the training data 104 can include a large database (e.g., hundreds or thousands) of 3D medical images (e.g., volumetric representations of an anatomical ROI generated from a plurality of 2D scan slices or the like) depicting the same or similar anatomical ROI with ground truth (GT) segmentation data. The GT segmentation data can include information associated with the respective 3D medical images that identifies or indicates the relative position and dimensions (e.g., geometry) of the object (or objects) of interest for segmentation within the 3D medical image. For instance, in one example implementation, the training data 104 can include 3D medical images of patients' chests and the GT segmentation data can include previously generated 3D segmentation masks defining the relative position and dimensions of the lungs in 3D.

Figure 3:
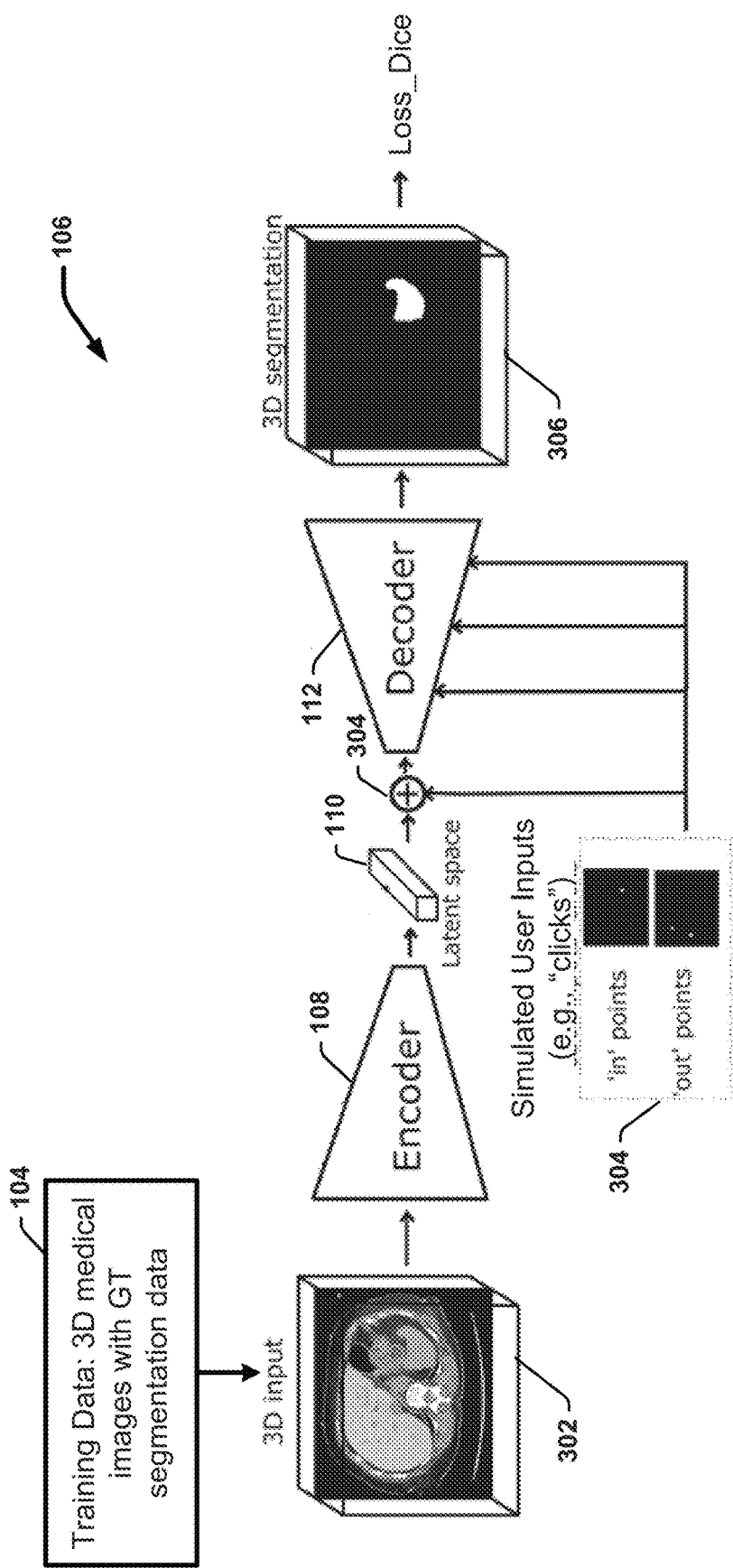
FIG. 3 illustrates an example training process for training an interactive segmentation model comprising an encoder network and a decoder network in accordance with one or more embodiments of the disclosed subject matter.

The model training process 106 is described in detail infra with reference to FIG. 3. At high level, the training process 106 involves training the encoder 108 to transform and compress the input 3D medical images into latent space 110. In this regard, the latent space 110 corresponds to compressed representations of the 3D medical images that includes a reduced set of key features extracted from the 3D medical images, wherein this reduced set of key features includes all the information needed to perform the segmentation of the corresponding 3D medical images. The training process 106 further involves training the decoder 112 to generate segmentation masks from the latent space representations based on simulated user input points. These simulated user input points are generated from the corresponding GT information provided for each of the training 3D medical images. In this regard, the disclosed systems and methods enables users to apply different mark-ups to a displayed 3D medical image (or portion thereof) marking an object or region of interest for segmenting. The mark-ups may be in the form of points, lines, circles, free-hand drawing tools and the like that indicate the boundary points of the object or region of interest for segmenting.

Figure 2:
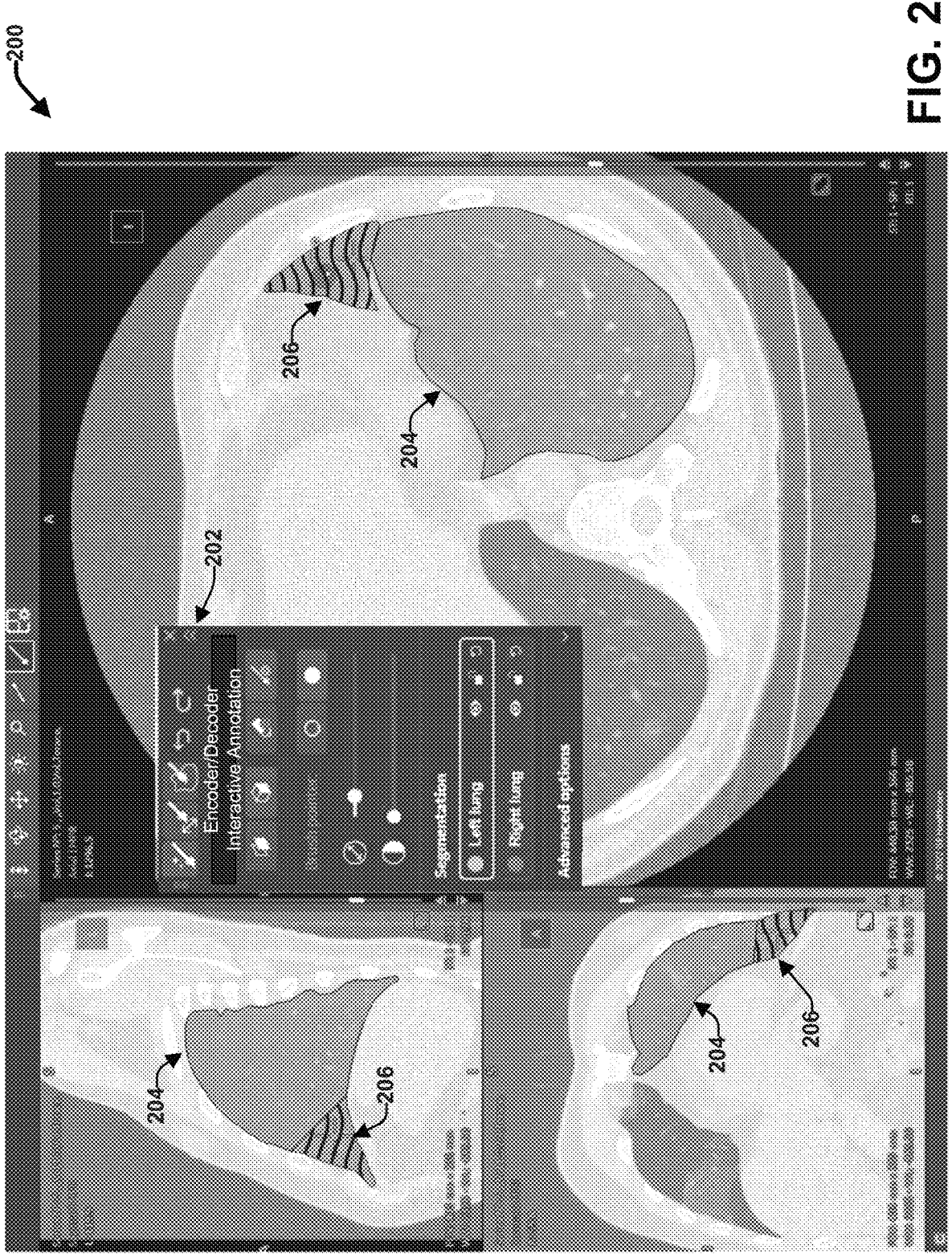
FIG. 2 presents an example graphical user interface of a medical imaging application in association with usage of an interactive 3D segmentation functionality in accordance with one or more embodiments of the disclosed subject matter.

For example, FIG. 2 presents an example GUI 200 of a medical imaging application in association with usage of an interactive 3D segmentation functionality in accordance with one or more embodiments of the disclosed subject matter. The GUI 200 includes three viewports respectively depicting different views or perspectives of a 3D medical image of a patient's chest generated from CT scan data of the patient's chest (e.g., upper left viewport: sagittal, lower left viewport: coronal, and primary larger viewport: axial). In this example, segmentation masks are provided as overlay data over the lungs as depicted in each viewport. In some implementations, these segmentation masks may have been automatically generated and applied by one or more existing 3D lung segmentation models. In other implementations, these segmentation mask may have been manually applied via the interactive segmentation tools provided by the underlying software. For example, in the embodiment shown, at least some of these interactive segmentation tools are provided via the interactive annotation dialog box 202. These segmentation tools provided by the interactive annotation dialog box 202 can allow the user to apply manual mark-ups to the displayed portion (or portions) of the 3D medical image either defining or marking an object for segmentation manually (e.g., from scratch) or correcting a model generated segmentation mask. The type of the manual mark-ups provided by interactive segmentation software can vary. For example, the marks-ups can be in the form of free-form lines and scribble, size controlled bounding boxes or circles, points or dots marking inside and outside regions of the object for segmentation, and so on.

In the embodiment shown, the user is employing the interactive segmentation tools to generate a segmentation of the left lung. The portion of the left lung defined by masked region 204 corresponds to the portion of the left lung that has already been defined and accepted using the 3D segmentation tools (or automatically via an existing lung segmentation model). The portion of the left lung defined by masked region 206 corresponds to a newly defined region to be added to the final left lung segmentation mask and applied by the user using the interactive 3D segmentation tools disclosed herein. This masked region 206 is shown with a patterned line fill to indicate that the masked region 206 is displayed in a "preview mode" and corresponds to a preview of the user defined segmented region. Upon selection of the masked region 206 in preview mode (e.g., by clicking/double clicking on the masked region 206 or the like), the masked region 206 will be added to segmentation mask of the left lung including masked region 204 and the patterned line fill will be replaced with solid fill.

As illustrated in FIG. 2, the interactive 3D segmentation tools apply the corresponding segmentation masks and mask previews applied in the primary viewport to each of the different views of the 3D medical image (provided in the other viewports) in real-time. To facilitate this end, the interactive segmentation tools must compute the 3D geometry and position of the user defined area for segmentation relative to the 3D volume image of the chest. As described infra, the disclosed techniques provide for allowing the user to apply the segmentation mark-ups and receive updated mask previews of the corresponding 3D segmentation masks as illustrated in FIG. 2 in real-time in a web-deployment architecture by deploying the computationally extensive segmentation calculations at the frontend (i.e., the client side).

In this regard, with reference again to FIG. 1, during model training at 106, simulated user inputs corresponding to different user applied mark-up points are concatenated to the latent space 110 before the decoding part. After the model training process 106 is completed, the learned encoder and decoder weights for the specific clinical application are then stored and applied for the online process 102. The online process 102 corresponds to an interactive 3D segmentation process (e.g., illustrated in FIG. 2 with reference to GUI 200) provided by a medical imaging application deployed as a web-based application access via a client device using a web-browser (e.g., a web-application, a hybrid application, a thin-client application, a thick-client application, a mobile application, etc.). In accordance with this deployment architecture, the features and functionalities of the medical imaging application, including the interactive 3D segmentation process, are distributed between a server device where the back-end processing 114 is performed, and a client device wherein the front-end processing 122 is performed. In particular, the trained version of the encoder (denoted as encoder 108' as opposed to encoder 108) is deployed and executed by the server device and the trained version of the decoder (denoted as decoder 120' as opposed to decoder 112) is deployed and executed by the client device. In this regard, the trained version of the encoder 108 corresponds to the encoder 108 with the learned encoder weights for the particular clinical application applied and the trained version of the decoder 112' correspond to the decoder 112 with the learned decoder weights for the particular clinical application applied.

The online process 102 assumes the user has launched the web-based medical imaging application using a client device and selected a 3D medical exam for performing 3D segmentation on. For example, assume the user is presented with a GUI similar to that of GUI 200 and is presented with one or more perspectives of a 3D volume representation of the captured anatomical ROI. The entirety of the 3D volume representation is stored at the server device (or a database accessible to the server device) and is represented in FIG. 1 as 3D medical image data 116. The online process 102 further assumes that the user has requested activation or initialization of the interactive 3D segmentation functionality of the medical imaging application (e.g., or this may be automatic in response to selection of a 3D imaging exam for reviewing).

In accordance with the backend processing 114, in response to initialization of the interactive 3D segmentation functionality (or selection of the 3D medical image data 116 by the user for processing), at 118, the backend server applies the encoder 108' to the 3D medical image data 116 (e.g., an input 3D medical image or input volume image) to convert the 3D input volume (or part of the volume) into a latent space representation 110' thereof: a small and compressed version of the 3D medical image data 116. At 120, the server then transfers (e.g., provides, transmits, sends, etc.) the latent space representation 110' and the corresponding decoder weights to the frontend client device for the frontend processing 122. From now on, the frontend client device has the required information to perform all the interactive edition of the segmentation mask.

In this regard, at 124 the user provides mark-up input to a displayed portion of the 3D medical image data indicating an object or region of the object included therein for segmenting. The type of the applied user mark-up data can vary and may include but is not limited to: one or more points inside the object, one or more points outside the object, one or more points or lines indicating a boundary of the object, free-hand lines or shapes on or around the object, guided lines or shapes on or around the object. For example, the mark-up input can include some guide marks on the displayed image, such as two set of points corresponding to one or more inner points and/or one or more outer points of the object to segment. However, the mark-up input it is not limited to points and can include for example, free-hand scribbles, lines, polygons and other shapes, points on the boundaries of the object and so on. At 126, the client device applies the decoder 112' to compute and generate a corresponding segmentation mask (e.g., segmentation mask update 128) based on the user input and using the latent representation 110' and renders the segmentation mask update 128 in real-time on all viewports. In this regard, each time the applies new input marking points, lines, etc. relative to the object to segment at 122, an updated segmentation mask is computed at 126 and displayed to the user in real-time using the decoder 112' wherein the input to the decoder 112' comprises the latent space representation 110' and the user input data provided by the user via the interactive mark-up tools. The decoder network output is a new 3D mask based on the new user input from which the segmentation mask updates can be deduced at 128. At 130, the updated segmentation mask can be rendered as an overlay over the displayed portion of the 3D medical image data, which corresponds to a preview image that the user can control in 3D (e.g., masked region 206 as described above with reference to FIG. 2). In this regard, each time the user applies new mark-up input, a new preview is shown to the user in real time. At 132, the user can choose to either accept the update or decline the update corresponding to the preview. Based on reception of input selecting the update, the client device can apply the segmentation at 134 corresponding to the preview. Based on reception of input declining the update, the client device can remove the most recently applied segmentation preview overlay data. Process 122 can further be repeated as many times desired by the user until the user is satisfied with the final segmentation.

FIG. 3 illustrates an example training process 106 for training the 3D segmentation model comprising the encoder 108 network and the decoder network 112 in accordance with one or more embodiments of the disclosed subject matter. As described above, the training data 104 for the model training process 106 can include a large collection (e.g., hundreds of thousands) of 3D medical images with GT segmentation data associated therewith. Each of the 3D medical images in the training data collection depict a same or similar anatomical region of interest and include GT data marking one or more objects or regions of interest previously segmented in 3D. The one or more object or regions may be similar or different depending on the clinical usage context. In this example, the input 3D medical images correspond to chest exams, however the specific type of the training data can vary for different clinical segmentation tasks (e.g., corresponding to different target object or regions for 3D segmentation). In this regard, different segmentation models can be generated using process 106 for different anatomical regions and different clinical segmentation tasks.

In accordance with training process 106, each 3D medical image 302 is processed separately and applied as input to the encoder 108. In one or more embodiments, the encoder 108 comprises a set of convolutions, residual connection and few max pooling layers that transform and compress each of the input 3D images into a latent space representation 110. This latent space representation is further concatenated with simulated user inputs at 304 generated from the corresponding GT segmentation data for each input 3D image. In particular, in some embodiments, at 304, using the GT segmentation data applied to each of the input 3D images, the training processes can generate two 3D volumes at the same spatial resolution as the latent space for each input 3D image. The first 3D volume can comprise a first set of points which are inside the object of interest and the second 3D volume can comprise second set of points which are outside the object. These inner and outer points can be generated from the GT segmentation data. In one or more embodiments, the decoder 112 employs gradient descent algorithm and these inner and outer points are randomly placed at each iteration of the gradient descent algorithm. In this regard, the inner and outer points are injected at each stage of the decoder 112. The output of the decoder 112 is a probability segmentation 306 that is compared to the corresponding GT segmentation using a suitable loss function, such as dice loss or another loss function. This generate gradients that are backpropagated into the decoder 112 and used to update the decoder network weights. Many iterations of this training loop are required until the convergence is reached. Once convergence has been reached, the learned encoder and decoder weights can be saved and stored in association with the encoder 108 and the decoder 112, resulting in the trained versions of the encoder 108' and the decoder 112' for the specific type of input 3D medical images and clinical segmentation task.

Figure 4:
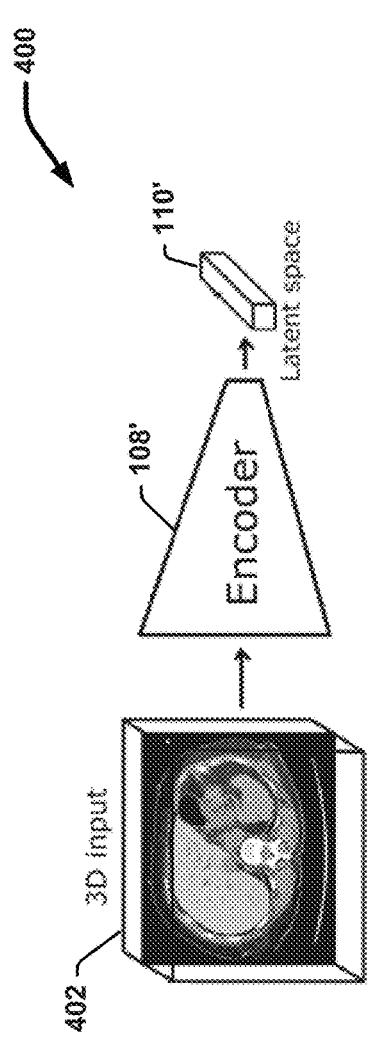
FIG. 4 illustrates an example backend processing task that facilitates interactive segmentation of medical images with low latency under a cloud-deployment architecture in accordance with one or more embodiments of the disclosed subject matter.

FIG. 4 illustrates an example backend online processing task 400 using the trained encoder 108' in accordance with one or more embodiments of the disclosed subject matter. With reference to FIGS. 1 and 4, the processing task 400 correspond to block 118 of the online process 102 performed by the server device. This processing task 400 is only performed once for each usage scenario. For example, in various embodiments, the server can perform the backend processing task 400 in response to initialization/activation of the 3D segmentation tool provided by the medical imaging application by the client device in association usage of the medical imaging application at the client device and a selected 3D medical image (e.g., a 3D imaging study/exam from which the 3D medical image/3D input volume was generated) for reviewing and segmenting in 3D. In this regard, the 3D input 402 corresponds to the selected 3D medical image, which corresponds to a new 3D input volume excluded from the training data. In accordance with the backend processing task 400, the server device employs the encoder 108' to generate a latent space representation 110' of the 3D input volume, which corresponds to a compressed version of the 3D input volume. In this regard, the encoder 108' employs a set of trained convolutions and pooling layers that extract a reduced subset of key features from the 3D input 402 and transpose these key features into the latent space representation 110'.

The latent space representation 110' contains all the information required to compute the 3D segmentation by the decoder 112'. As illustrated in FIG. 1, the latent space representation is then sent by the server device (e.g., transmitted via a network) to the frontend client device (i.e., the computer of the user) for usage by the decoder 112' deployed at the client device. In some embodiments, the decoder network deployed at the client device can include a default decoder employing the same architecture as the decoder 112 with weights set to default values. With these embodiments, in association with sending the latent space representation 110' the server device can also send the corresponding decoder weights to the client device for the trained decoder 112' paired with the trained encoder 108' for the specific type of input 3D image and clinical segmentation task. The client device can further replace the default weights with the received weights prior execution of the decoder 112' at the client device. Alternatively, the decoder network deployed at the client device can be preconfigured with the learned decoder weights for the specific type of input 3D image and clinical segmentation task.

Figure 5:
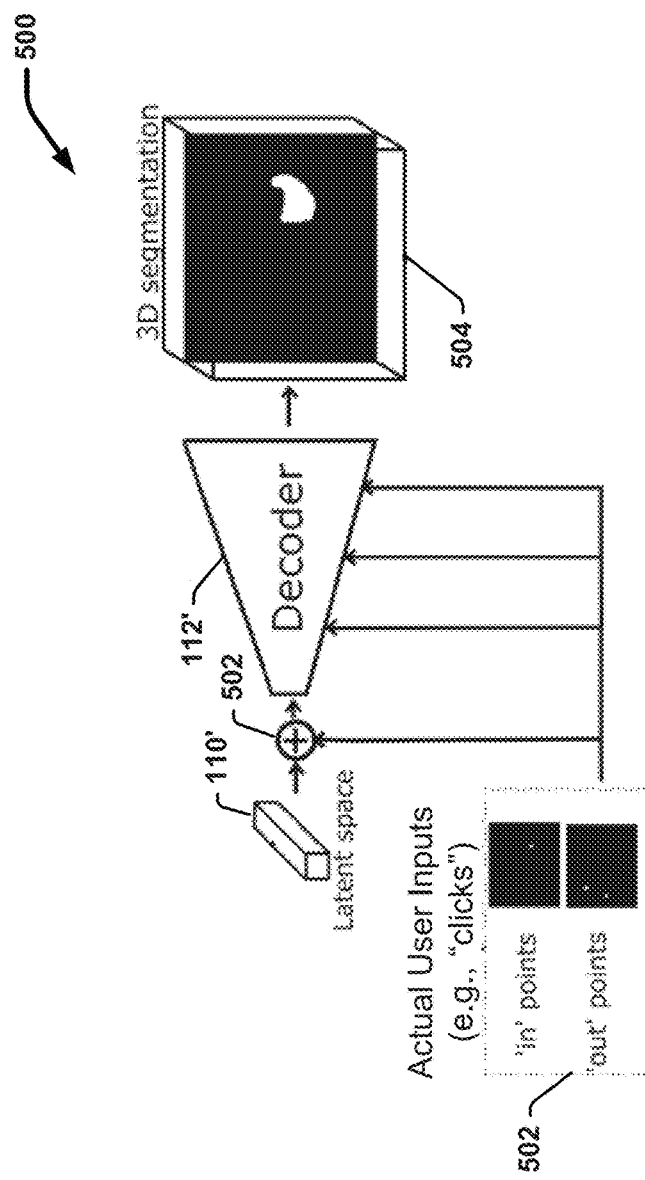
FIG. 5 illustrates an example frontend processing task that facilitates interactive segmentation of medical images with low latency under a cloud-deployment architecture in accordance with one or more embodiments of the disclosed subject matter.

FIG. 5 illustrates an example frontend online processing task 500 using the trained decoder 108' in accordance with one or more embodiments of the disclosed subject matter. With reference to FIGS. 1 and 5, the processing task 500 correspond to blocks 124, 126 and 128 of the frontend processing 122 performed by the client device. As described with reference to FIG. 1, this processing task 500 can be repeated each time the user provides new mark-up input indicating an object or region of an object for segmentation on a displayed portion of the 3D input volume 104. In this regard, at 502, the user can apply some mark-up guides on the displayed image indicating the object or the region of the object for segmentation. For instance, similar to the simulated user input data, the user applied mark-up guides may include one or more sets of points on the image indicating one or more inner points and/or one or more outer points of the object to segment. However, the user applied mark-up guides is not limited to points and can include various other forms of mark-up input, such as free-hand or guided lines, shapes, points or lines indicating the boundary of the object, and so on. At 502, these guides are converted to 3D volumes that are injected at all the stages of the decoder 112'. From the latent space representation 110' and the set of guides, the decoder 112' generates a segmentation mask 504 of the desired object. This frontend calculation can be computed by the client device using a suitable graphics processing unit (GPU) and can run in real-time using the client device's local computer graphic card (e.g., webGL, OpenGL, tensorFlow.js, and the like).

Figure 6:
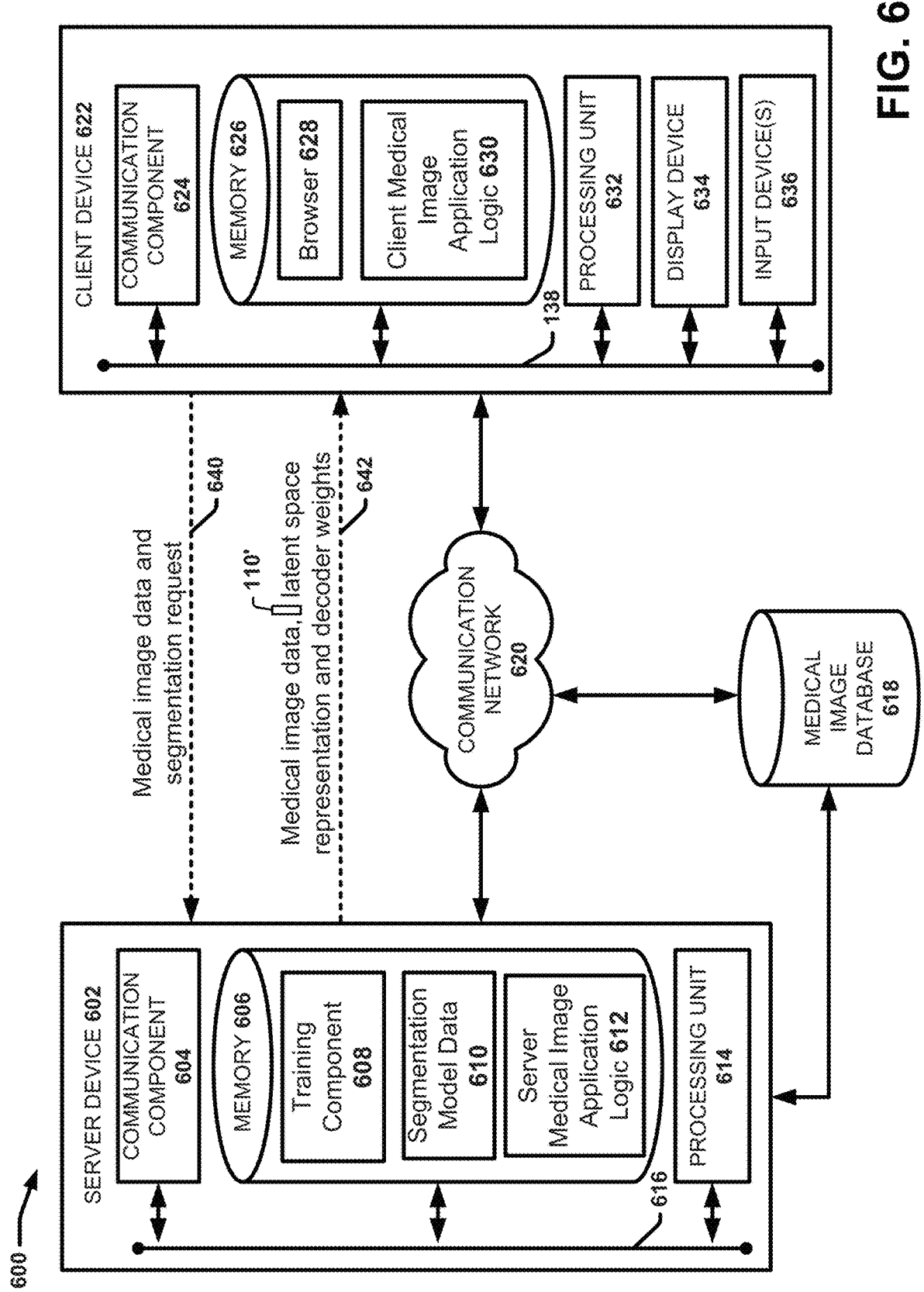
FIG. 6 illustrates a block diagram of an example, non-limiting system that facilitate interactive segmentation of medical images with low latency under a cloud-deployment architecture in accordance with one or more embodiments of the disclosed subject matter.

FIG. 6 illustrates a block diagram of an example, non-limiting system 600 that facilitate interactive segmentation of medical images with low latency under a cloud-deployment architecture in accordance with one or more embodiments of the disclosed subject matter. In particular, system 600 illustrates an example deployment architecture in which one or more of the feature and functionalities of the processes and techniques described with reference to FIGS. 1-5 may be implemented. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

With reference to FIGS. 1-6, system 600 includes a server device 102 that can be employed to perform the training process 101 and the backend processing 114 described with reference to process 100 (as well as training process 300 and backend processing task 400), and a client device 622 that can be employed to perform the frontend processing 122 described with reference to process 100 (as well as frontend processing task 500). The server device 602 and the client device 622 can be communicatively coupled via a communication network 620 (e.g., the Internet, or another type of communication network). The server device 602 includes communication component 104 for communicating with the client device 622 (via communication component 624) via the communication network 620. The client device similarly includes communication component 624 for communicating with the server device 602 (via communication 604) via the communication network. In this regard, communication component 604 and communication component 624 can respectively include suitable hardware and/or software that enables communication between the respective devices via the communication network 620.

The server device 602 can further include (or be operatively coupled to) at least one memory 608 that stores computer/machine executable components or instructions (and other described herein) that facilitate the training process 101 and the backend processing 114 described with reference to process 100 (as well as training process 300 and backend processing task 400) described above. In particular, the training component 608 can be employed by the server device 602 to perform the training process 101 and/or training process 300. Additionally, or alternatively, the training component 608 and the 3D segmentation model training may be deployed and executed by another device or system. The segmentation model data 610 can include trained and untrained versions of the 3D segmentation model (e.g., comprising the encoder 108 and decoder 112, and the encoder 108' and the decoder 112'). As described above, in some embodiments, different versions of the 3D segmentation model can be trained to perform different clinical segmentation tasks for different anatomical ROIs, different types of 3D medical images (e.g., corresponding to different anatomical ROIs and/or capture modalities), and/or different objects or ROIs for segmentation. With these embodiments, the segmentation model data 610 can include information that uniquely identifies each of the different 3D segmentation models and their corresponding clinical segmentation task, the type of 3D medical image data they are configured to process, and their corresponding trained versions of the encoder 108' and their decoder 112' and/or their learned encoder and decoder weights. The server medical image application logic 612 can include the server-side instructions that define the operations described with respect to the backend processing 114 described with reference to process 100 and the backend processing task 400 described above. Additional details regarding the server medical image application logic 612 are described below with reference to FIG. 7.

The server device 602 can further include (or be operatively coupled to) at least one processing unit 614 that executes the computer/machine executable components or instructions stored in the memory 608 (and the communication component 604). The server device 602 further includes a device bus 616 that operatively couples the respective components of the server device to one another (e.g., the communication component 604, the memory 606 and the processing unit 614). The server device can further include (or be communicatively and/or operatively coupled to, (e.g., directly and/or via the communication network 620), medical image database 618. The medical image database 618 can store the training 3D medical images and/or a collection of additional 3D medical images and associated metadata for streaming to the client device 622 and processing via the server medical image application logic 612 and/or the client medical image application logic 630.

The client device 622 can further include (or be operatively coupled to) at least one memory 626 that stores computer/machine executable components or instructions, including browser 628 (e.g., corresponding to a webbrowser), and client medical image application logic 630 (and other described herein) that facilitate the frontend processing 122 described with reference to process 100 and frontend processing task 500 described with reference to FIG. 5. In this regard, the client medical image application logic 612 can include the client-side instructions that define the operations described with respect to the frontend processing 122 described with reference to process 100 and the frontend processing task 500 described above. The browser 628 can provide for accessing and communicating with the server medical image application logic 612 via the communication network 620. Additional details regarding the client medical image application logic 630 are also described below with reference to FIG. 7. The client device 622 further includes a display device 634 that provides for rendering and displaying the GUI (e.g., GUI 200 or the like) of the medical imaging application (provided by the server medical image application logic 612 and the client medical image application logic 630) and the features and functionalities of the associated interactive 3D segmentation tools described herein. The client device further includes one or more input device 636 that provide for receiving user input in association usage of the medical imaging application and the features and functionalities of the associated interactive 3D segmentation tools described herein. The client device 622 further includes a device bus that operatively couples the respective elements/components of the client device to one another (e.g., the communication component 624, the memory 626, the processing unit 632, the display device 634, and the one or more input device 636). Examples of said and memory (memory 606 and memory 628), processing unit (614 and processing unit 662), display device 634 and input device 636 as well as other suitable computer or computing-based elements, can be found with reference to FIG. 11, and can be used in connection with implementing one or more of the systems or components shown and described in connection with FIG. 6 or other figures disclosed herein.

In various embodiments, the server medical image application logic 612 and the client medical image application logic 630 in combination correspond to a distributed medical imaging application that facilitates accessing and viewing medical image data provided in the medical image database 618 by the client device (e.g., using browser 628) and performing interactive 3D segmentation on the displayed medical image data. For example, the distributed application can be web-based application, such as a web-application, a thin client application, a thick client application, a hybrid application, a mobile application, and the like. (e.g., utilizing a browser 124). In this regard, the client device 622 can make medical image data and segmentation request 640 to the server device 620 using the browser and the client medical image application logic 630. The medical image data and segmentation request can include information identifying or indicating a specific 3D medical image for viewing and/or segmenting using the interactive 3D segmentation tools of the medical imaging application. In some implementations, the requests 640 can also include information identifying or indicating a specific clinical segmentation task (to facilitate selection of the appropriate 3D segmentation model) to be applied. In some implementations, the request 640 can be automatically generated by the client device (e.g., via the client medical image application logic 630 in response to initiation of the medical imaging application and selection of a 3D medical image for viewing and/or in response to initiation of the 3D segmentation functionality of the medical imaging application). In response to a received request 640, (using the server medical image application logic 612) the server device retrieves the selected 3D medical image (e.g., from the medical image database 618), selects the appropriate 3D segmentation model for application to the 3D medical image as stored in the segmentation model data 610, executes the processing task 400 using 3D medical image and the corresponding encoder 108' to generate the latent space representation 110' and sends (e.g., streams or transmits) the 3D medical image data (or portions thereof), the latent space representation 110' and the corresponding decoder 112' weights to the client device as response data 642. The client device 622 thereafter executes the backend processing task 500 using the latent space representation 110' and the decoder 108' with the applied decoder weights.

Figure 7:
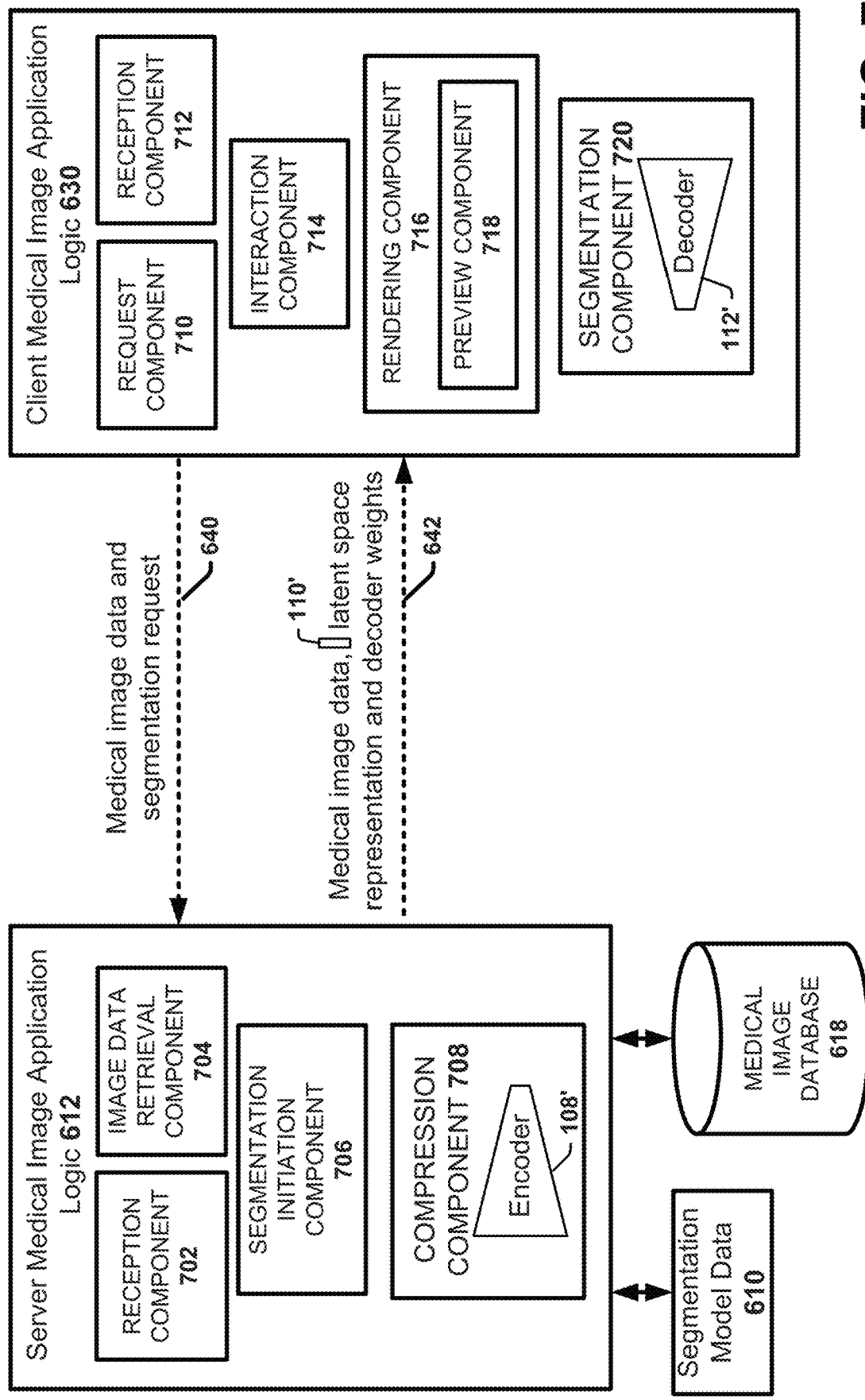
FIG. 7 illustrates respective components of the server and client medical image application logic in accordance with one or more embodiments of the disclosed subject matter.

FIG. 7 illustrates respective components of the server and client medical image application logic in accordance with one or more embodiments of the disclosed subject matter. Repetitive description of like elements employed in respective embodiments is omitted for sake of brevity.

The server medical image application logic 612 includes several computer/machine executable components or instructions (and other described herein) that facilitate backend processing 114 described with reference to process 100 and/or backend processing task 400 described above. The components include reception component 702, image data retrieval component 704 segmentation initiation component 706 and compression component 708 and encoder 108'. The reception component 702 can receive the medical image data and segmentation requests 640 sent by client medical imaging application logic 626 (e.g., via request component 710) and the client device 622 (e.g., using communication component 624 and/or browser 626). Based on and/or in response to reception of a medical image data and segmentation request 640, the image data retrieval component 704 can retrieve the corresponding 3D medical image data associated with the request (e.g., a 3D input volume and associated 2D/3D image data and metadata) from the medical image database (e.g., using information included in the request 640 identifying or indicating the specific 3D medical image data study/exam for viewing and segmenting at the client device 622). The segmentation initiation component 706 can further initiate or active that 3D segmentation functionality of the client medical imaging application logic by performing the frontend processing task or tasks described herein (e.g., frontend processing task 400 or the like).

In this regard, in implementations in which different 3D segmentation models have been developed for different types of 3D medical images and/or 3D segmentation tasks, the segmentation initiation component 706 can select the appropriate 3D segmentation model for applying to the 3D medical image data as stored in the segmentation model data 610 (e.g., based on the type of the 3D medical image data selected and/or information received with the request indicating the specific 3D segmentation task to be applied). In other implementations in which the system (e.g., system 600) is tailored for a single type of medical image data and segmentation task, this step can be skipped. The compression component 708 can further apply the corresponding encoder weights for the appropriate 3D segmentation model to the encoder 108' and generate the latent space representation 110' of the 3D medical image using the encoder 108' with the appropriate weights. The segmentation initiation component 706 can also retrieve the corresponding model's decoder weights (e.g., as stored in the segmentation model data 610). The segmentation initiation component 706 can further respond to the request 640 by sending (e.g., transmitting via the communication network 620, using communication component 604) the client device 622 with response data 642, the response data comprising at least the latent space representation 610', and in some implementations, the corresponding weights for the decoder 112' and the medical image data requested for segmenting (or portions thereof). Upon reception of the medical image data (or portions thereof), the client medical image application logic 630 can activate the interactive 3D segmentation functionality of the medical imaging application and display selected portions of the received medical image data (e.g., in one or more viewports, as illustrated in FIG. 2 and GUI 200).

The client medical image application logic 630 includes several computer/machine executable components or instructions (and other described herein) that facilitate frontend processing 122 described with reference to process 100 and/or frontend processing task 500 described above. These components include request component 710, reception component 712, interaction component 714, rendering component 716, preview component 718, segmentation component 720 and decoder 112'. The request component 710 can facilitate generating and sending the medical image data and segmentation requests 640 to the server device 602 (e.g., via communication component 624 using the browser 626). For example, in various embodiments, the request component 710 can generate and send the requests 640 in response to reception of user input via the application (e.g., via interaction component 714) selecting a 3D medical image study/ exam for viewing and segmenting using the interactive segmentation tools of the application. The reception component 702 can receive the response data 642 from the server device 602 in response to sending of the request 640. Upon reception of the medical image data (or portions thereof), the client medical image application logic 630 can activate the interactive 3D segmentation functionality of the medical imaging application and display selected portions of the received medical image data (e.g., in one or more viewports, as illustrated in FIG. 2 and GUI 200).

The interaction component 714 can provide the interactive mark-up tools associated with the interactive segmentation functionality. In this regard, the interaction component 714 can receive or facilitate receiving user input relative to a displayed portion (e.g., as displayed via the rendering component 716) of the 3D medical image data indicating an object or region of an object for segmenting (e.g., via the interactive annotation dialog box 202 or the like). Based on the reception of the applied user mark-up data, the segmentation component 720 can generate a corresponding segmentation mask using the decoder 112' with the applied appropriate decoder weights. The preview component 718 can further generate and render the segmentation mask as overlay data over the object and the displayed portion of the 3D medical image in a preview mode (as described with reference to frontend processing 122). The interaction component 714 can further receive additional user input relative to the displayed portion of the 3D medical image indicating the object included in the displayed portion for updated segmentation, and the segmentation component 720 can generate an updated segmentation mask for the object based on the new user input using the compressed representation and the decoder network 112', and the preview component 718 can renders the updated segmentation mask as new overlay data over the object and the displayed portion of the 3D medical image in real-time. In this manner, the system (e.g., system 600) provides for real-time interactive segmentation of the 3D medical image in which the user can repeatedly apply mark-ups to the displayed 3D medical image indicating an object or region of the object for segmentation and be presented with updated segmentation masks based on the mark-ups in real-time, wherein the computationally extensive 3D segmentation calculations are performed at the client side by the decoder network 112' using the same latent space representation 110' received from the server device 102.

Figure 8:
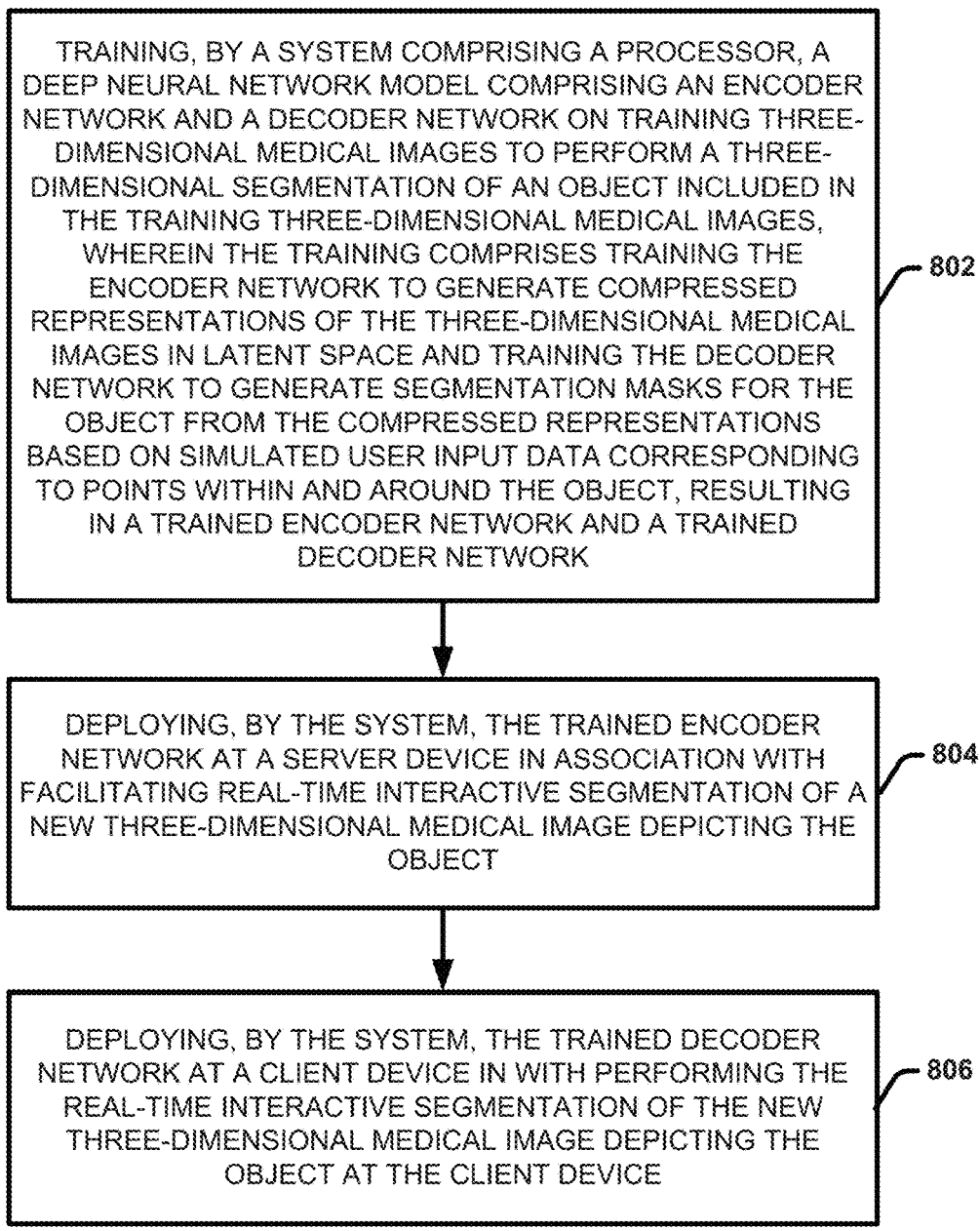
FIG. 8 illustrates a block diagram of an example, non-limiting computer implemented method that facilitates interactive segmentation of medical images with low latency under a cloud-deployment architecture in accordance with one or more embodiments of the disclosed subject matter.

FIG. 8 illustrates a block diagram of an example, non-limiting computer implemented method 800 that facilitates interactive segmentation of medical images with low latency under a cloud-deployment architecture in accordance with one or more embodiments of the disclosed subject matter. Repetitive description of like elements employed in respective embodiments is omitted for sake of brevity.

Method 800 comprise, at 802, training, by a system comprising a processor (e.g., system 500 or another system using training component 608), a deep neural network model comprising an encoder network and a decoder network on training 3D medical images to perform a three-dimensional segmentation of an object included in the training three-dimensional medical images, wherein the training comprises training the encoder network (e.g., encoder 108) to generate compressed representations of the 3D medical images in latent space and training the decoder network (e.g., decoder 112) to generate segmentation masks for the object from the compressed representations based on simulated user input data corresponding to points within (e.g., inner points) and around the object (e.g., outer points), resulting in a trained encoder network (e.g., encoder 108') and a trained decoder network (e.g., decoder 112'). At 804, method 800 comprises deploying, by the system, the trained encoder network at a server device (e.g., server device 602) in association with facilitating real-time interactive segmentation of a new 3D medical image depicting the object. At 806, method 800 further comprises deploying, by the system, the trained decoder network at a client device (e.g., client device 622) in with performing the real-time interactive segmentation of the new 3D medical image depicting the object at the client device.

Figure 9:
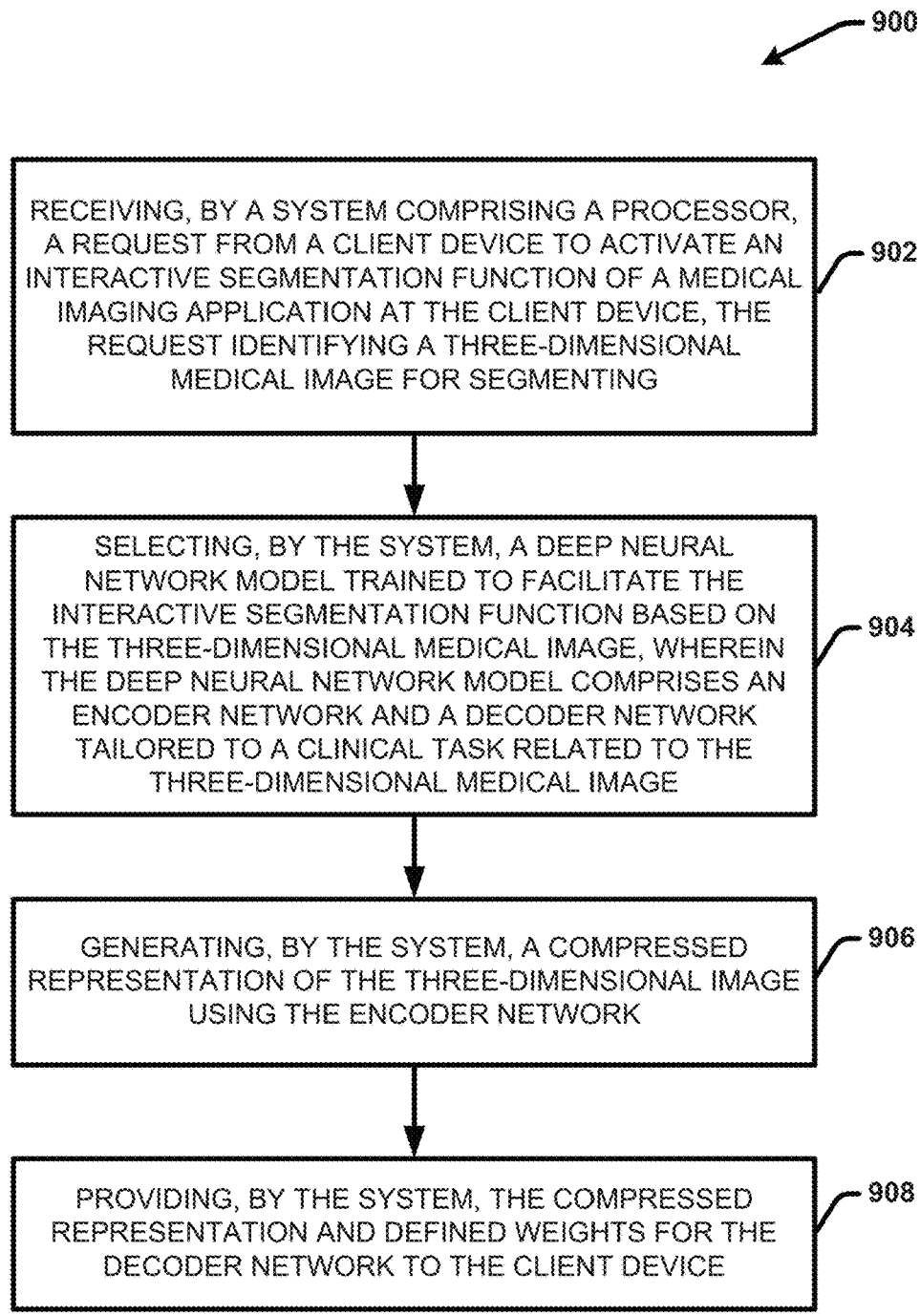
FIG. 9 illustrates a block diagram of another example, non-limiting computer implemented method that facilitates interactive segmentation of medical images with low latency under a cloud-deployment architecture in accordance with one or more embodiments of the disclosed subject matter.

FIG. 9 illustrates a block diagram of another example, non-limiting computer implemented method 900 that facilitates interactive segmentation of medical images with low latency under a cloud-deployment architecture in accordance with one or more embodiments of the disclosed subject matter. Method 900 corresponds to a backend process that can be performed by the server device 602 in accordance with the backend processing 114 of the online process 102 and backend processing task 400. Repetitive description of like elements employed in respective embodiments is omitted for sake of brevity.

At 902, method 900 comprises, receiving (e.g., via reception component 702 and/or communication component 604), by a system comprising a processor (e.g., system 600 and/or server device 602), a request (e.g., medical image data and segmentation request 640) from a client device (e.g., client device 622) to activate an interactive segmentation function of a medical imaging application at the client device, the request identifying a 3D medical image for segmenting. At 904, method 900 comprises selecting, by the system (e.g., via segmentation initiation component 706), a deep neural network model trained to facilitate the interactive segmentation function based on the three-dimensional medical image, wherein the deep neural network model comprises comprising an encoder network and a decoder network tailored to a clinical task related to the three-dimensional medical image. For example, the segmentation initiation component 706 can select a previously trained encoder/ decoder segmentation model included in the segmentation model data 610 that was trained to perform segmentation for the type of the 3D medical image. The information included in the segmentation model data 610 can include at least the trained encoder network (e.g., encoder 108') for the type of the 3D medical image and the corresponding decoder network weights. In some implementations, the model may also be tailored to perform a specific type of segmentation (e.g., for a specific object, ROI, plane, etc.). With these implementations, the request may also indicate the desired type of clinical segmentation to be performed relative to the 3D medical image by the interactive segmentation function. At 906, method 900 comprises generating, by the system, a compressed representation of the 3D medical image using the encoder network (e.g., via compression component 708). At 908, method 900 comprises providing, by the system, the compressed representation and defined weights for the decoder network to the client device (e.g., via communication component 604).

Figure 10:
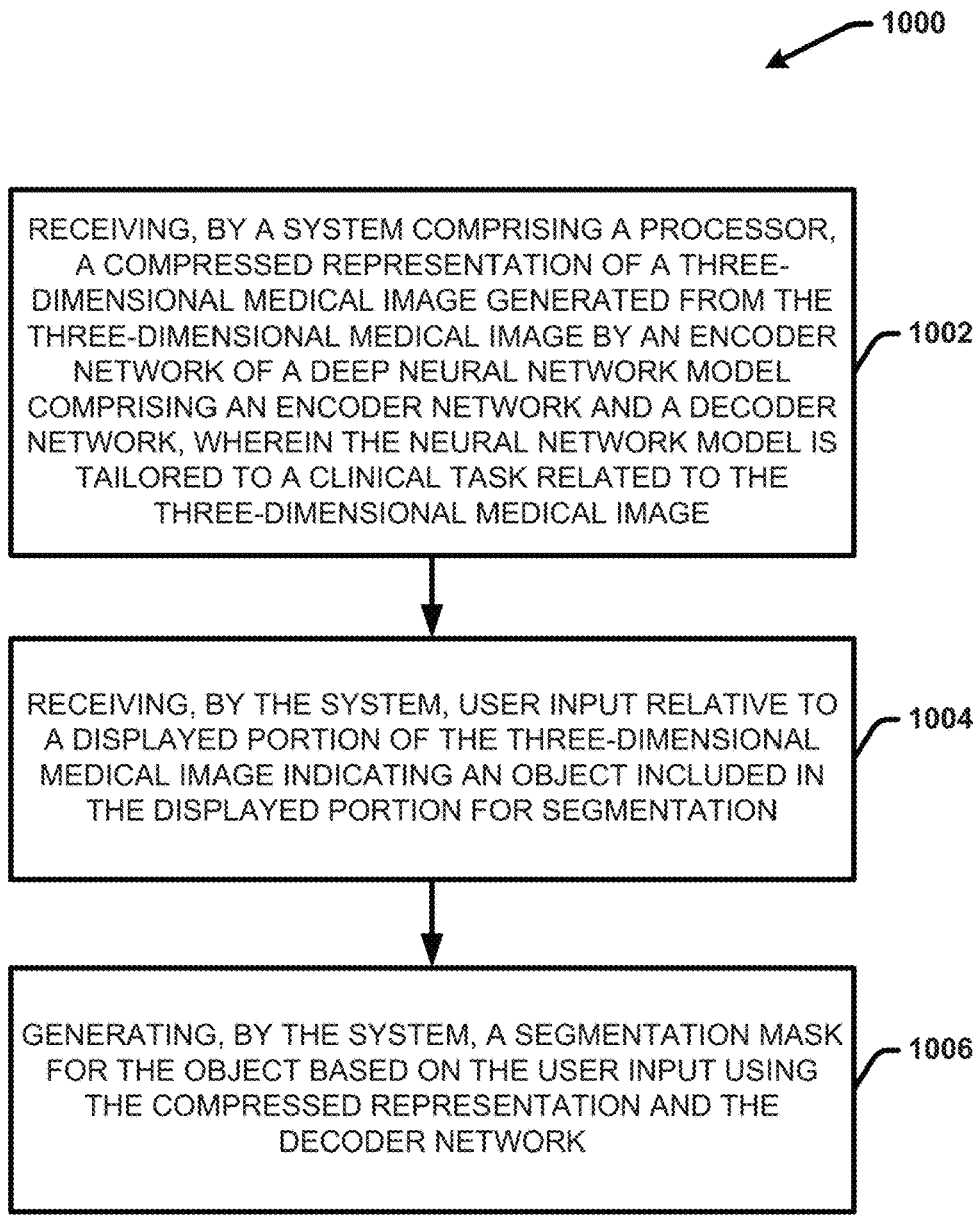
FIG. 10 illustrates a block diagram of another example, non-limiting computer implemented method that facilitates interactive segmentation of medical images with low latency under a cloud-deployment architecture in accordance with one or more embodiments of the disclosed subject matter.

FIG. 10 illustrates a block diagram of another example, non-limiting computer implemented method 1000 that facilitates interactive segmentation of medical images with low latency under a cloud-deployment architecture in accordance with one or more embodiments of the disclosed subject matter. Method 1000 corresponds to a frontend process that can be performed by the client device 622 in accordance with the frontend processing 122 of the online process 102 and frontend processing task 500. Repetitive description of like elements employed in respective embodiments is omitted for sake of brevity.

At 1002, method 1000 comprises receiving (e.g., via reception component 710 and/or communication component 624), by a system comprising a processor (e.g., client device 622 and/or system 600), a compressed representation (e.g., latent space representation 110') of a 3D medical image generated from the 3D medical image by an encoder network (e.g., encoder 108') of a deep neural network model comprising an encoder network and a decoder network, wherein the neural network model is tailored to a clinical task related to the 3D medical image. At 1004, method 1000 comprises receiving, by the system (e.g., via interaction component 714), user input relative to a displayed portion of the 3D medical image indicating an object included in the displayed portion for segmentation. The type of the applied user mark-up data can vary and may include but is not limited to: one or more points inside the object, one or more points outside the object, one or more points or lines indicating a boundary of the object, free-hand lines or shapes on or around the object, guided lines or shapes on or around the object. For example, the mark-up input can include some guide marks on the displayed image, such as two set of points corresponding to one or more inner points and/or one or more outer points of the object to segment. However, the mark-up input it is not limited to points and can include for example, free-hand scribbles, lines, polygons and other shapes, points on the boundaries of the object and so on. At 1006, method 1000 comprises generating, by the system, a segmentation mask for the object based on the user input using the compressed representation and the decoder network (e.g., via the segmentation component 720).

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, procedural programming languages, such as the "C" programming language or similar programming languages, and machine-learning programming languages such as like CUDA, Python, Tensorflow, PyTorch, and the like. The computer readable program instructions can execute entirely on the user's computer, partly on the user's computer, as a stand-alone software package, partly on the user's computer and partly on a remote computer or entirely on the remote computer or server using suitable processing hardware. In the latter scenario, the remote computer can be connected to the user's computer through any type of network, including a local area network (LAN) or a wide area network (WAN), or the connection can be made to an external computer (for example, through the Internet using an Internet Service Provider). In various embodiments involving machine-learning programming instructions, the processing hardware can include one or more graphics processing units (GPUs), central processing units (CPUs), and the like. For example, one or more of the encoder network 108' and/or the decoder network 112' may be written in a suitable machine-learning programming language and executed via one or more GPUs, CPUs or combinations thereof. In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 11, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 11:
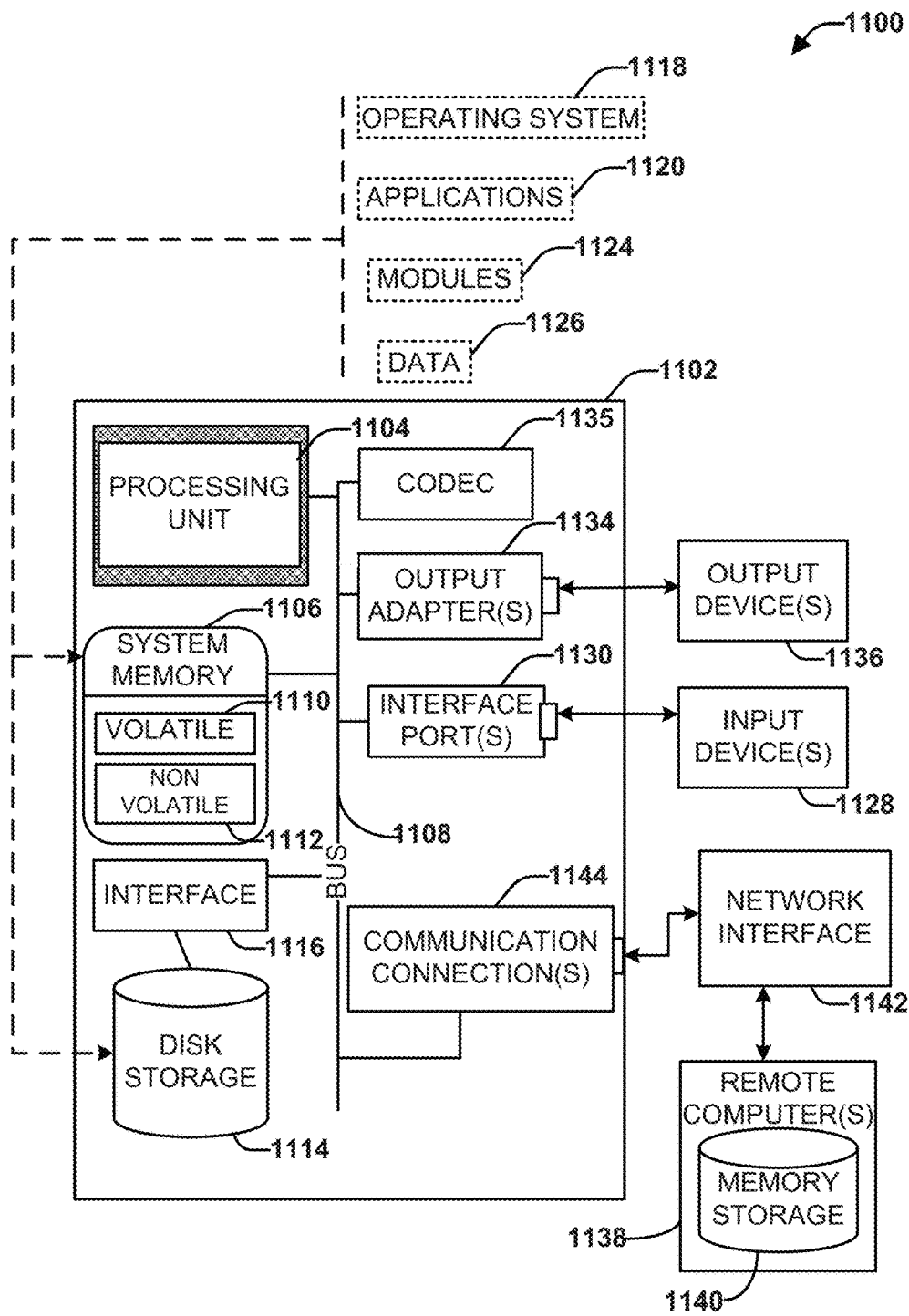
FIG. 11 illustrates a block diagram of an example, non-limiting operating environment in which one or more embodiments described herein can be facilitated.

With reference to FIG. 11, an example environment 1100 for implementing various aspects of the claimed subject matter includes a computer 1102. The computer 1102 includes a processing unit 1104, a system memory 1106, a codec 1135, and a system bus 1108. The system bus 1108 couples system components including, but not limited to, the system memory 1106 to the processing unit 1104. The processing unit 1104 can be any of various available processors. Dual microprocessors and other multiprocessor architectures also can be employed as the processing unit 1104.

The system bus 1108 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13114), and Small Computer Systems Interface (SCSI).

The system memory 1106 includes volatile memory 1110 and non-volatile memory 1112, which can employ one or more of the disclosed memory architectures, in various embodiments. The basic input/output system (BIOS), containing the basic routines to transfer information between elements within the computer 1102, such as during start-up, is stored in non-volatile memory 1112. In addition, according to present innovations, codec 1135 can include at least one of an encoder or decoder, wherein the at least one of an encoder or decoder can consist of hardware, software, or a combination of hardware and software. Although, codec 1135 is depicted as a separate component, codec 1135 can be contained within non-volatile memory 1112. By way of illustration, and not limitation, non-volatile memory 1112 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1112 can employ one or more of the disclosed memory devices, in at least some embodiments. Moreover, non-volatile memory 1112 can be computer memory (e.g., physically integrated with computer 1102 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1110 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1102 can also include removable/non-removable, volatile/non-volatile computer storage medium. FIG. 11 illustrates, for example, disk storage 1114. Disk storage 1114 includes, but is not limited to, devices like a magnetic disk drive, solid state disk (SSD), flash memory card, or memory stick. In addition, disk storage 1114 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1114 to the system bus 1108, a removable or non-removable interface is typically used, such as interface 1116. It is appreciated that disk storage 1114 can store information related to an entity. Such information might be stored at or provided to a server or to an application running on an entity device. In one embodiment, the entity can be notified (e.g., by way of output device(s) 1136) of the types of information that are stored to disk storage 1114 or transmitted to the server or application. The entity can be provided the opportunity to opt-in or opt-out of having such information collected or shared with the server or application (e.g., by way of input from input device(s) 1128).

It is to be appreciated that FIG. 11 describes software that acts as an intermediary between entities and the basic computer resources described in the suitable operating environment 1100. Such software includes an operating system 1118. Operating system 1118, which can be stored on disk storage 1114, acts to control and allocate resources of the computer system 1102. Applications 1120 take advantage of the management of resources by operating system 1118 through program modules 1124, and program data 1126, such as the boot/shutdown transaction table and the like, stored either in system memory 1106 or on disk storage 1114. It is to be appreciated that the claimed subject matter can be implemented with various operating systems or combinations of operating systems.

An entity enters commands or information into the computer 1102 through input device(s) 1128. Input devices 1128 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1104 through the system bus 1108 via interface port(s) 1130. Interface port(s) 1130 include, for example, a serial port, a parallel port, a game port, and a universal serial bus (USB). Output device(s) 1136 use some of the same type of ports as input device(s) 1128. Thus, for example, a USB port can be used to provide input to computer 1102 and to output information from computer 1102 to an output device 1136. Output adapter 1134 is provided to illustrate that there are some output devices 1136 like monitors, speakers, and printers, among other output devices 1136, which require special adapters. The output adapters 1134 include, by way of illustration and not limitation, video and sound cards that provide a means of connection between the output device 1136 and the system bus 1108. It should be noted that other devices or systems of devices provide both input and output capabilities such as remote computer(s) 1138.

Computer 1102 can operate in a networked environment using logical connections to one or more remote computers, such as remote computer(s) 1138. The remote computer(s) 1138 can be a personal computer, a server, a router, a network PC, a workstation, a microprocessor based appliance, a peer device, a smart phone, a tablet, or other network node, and typically includes many of the elements described relative to computer 1102. For purposes of brevity, only a memory storage device 1140 is illustrated with remote computer(s) 1138. Remote computer(s) 1138 is logically connected to computer 1102 through a network interface 1142 and then connected via communication connection(s) 1144. Network interface 1142 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1144 refers to the hardware/software employed to connect the network interface 1142 to the bus 1108. While communication connection 1144 is shown for illustrative clarity inside computer 1102, it can also be external to computer 1102. The hardware/software necessary for connection to the network interface 1142 includes, for exemplary purposes only, internal and external technologies such as, modems including regular telephone grade modems, cable modems and DSL modems, ISDN adapters, and wired and wireless Ethernet cards, hubs, and routers.

The illustrated aspects of the disclosure may also be practiced in distributed computing environments where certain tasks are performed by remote processing devices that are linked through a communications network. In a distributed computing environment, program modules can be located in both local and remote memory storage devices.

Figure 12:
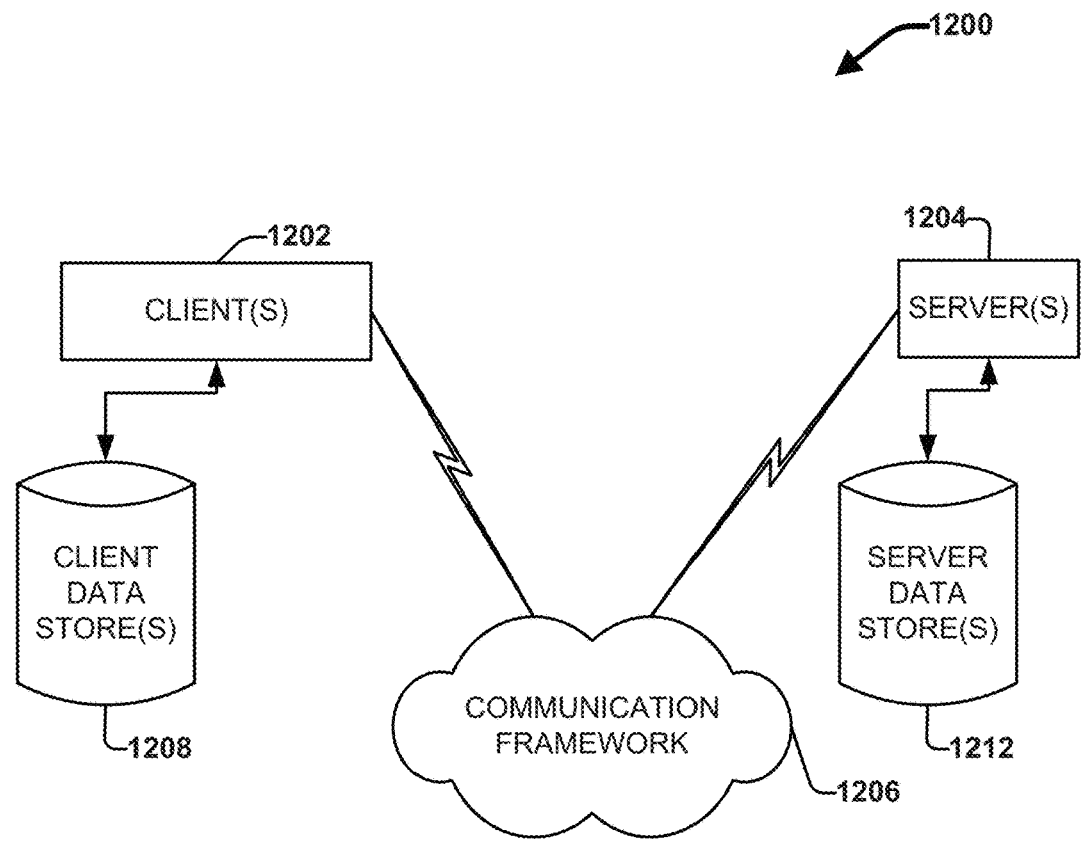
FIG. 12 illustrates a block diagram of another example, non-limiting operating environment in which one or more embodiments described herein can be facilitated.

Referring to FIG. 12, there is illustrated a schematic block diagram of a computing environment 1200 in accordance with this disclosure in which the subject systems (e.g., system 600 and the like), methods and computer readable media can be deployed. The computing environment 1200 includes one or more client(s) 1202 (e.g., laptops, smart phones, PDAs, media players, computers, portable electronic devices, tablets, and the like). The client(s) 1202 can be hardware and/or software (e.g., threads, processes, computing devices). The computing environment 1200 also includes one or more server(s) 1204. The server(s) 1204 can also be hardware or hardware in combination with software (e.g., threads, processes, computing devices). The servers 1204 can house threads to perform transformations by employing aspects of this disclosure, for example. In various embodiments, one or more components, devices, systems, or subsystems of system 400 can be deployed as hardware and/or software at a client 1202 and/or as hardware and/or software deployed at a server 1204. One possible communication between a client 1202 and a server 1204 can be in the form of a data packet transmitted between two or more computer processes wherein the data packet may include healthcare related data, training data, AI models, input data for the AI models, encrypted output data generated by the AI models, and the like. The data packet can include a metadata, e.g., associated contextual information, for example. The computing environment 1200 includes a communication framework 806 (e.g., a global communication network such as the Internet, or mobile network(s)) that can be employed to facilitate communications between the client(s) 1202 and the server(s) 1204.

Communications can be facilitated via a wired (including optical fiber) and/or wireless technology. The client(s) 122 include or are operatively connected to one or more client data store(s) 1208 that can be employed to store information local to the client(s) 1202 (e.g., the client medical image application logic 630). Similarly, the server(s) 1204 are operatively include or are operatively connected to one or more server data store(s) 812 that can be employed to store information local to the servers 1204 (e.g., the server medical image application logic 612, the segmentation model data 510, the medical image database 518, etc.)

In one embodiment, a client 1202 can transfer an encoded file, in accordance with the disclosed subject matter, to server 1204. Server 1204 can store the file, decode the file, or transmit the file to another client 1202. It is to be appreciated, that a client 1202 can also transfer uncompressed file to a server 1204 can compress the file in accordance with the disclosed subject matter. Likewise, server 1204 can encode video information and transmit the information via communication framework 1206 to one or more clients 1202.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "subsystem" "platform," "layer," "gateway," "interface," "service," "application," "device," and the like, can refer to and/or can include one or more computer-related entities or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in the memory, wherein the computer executable components comprise:
a decoder network;
a reception component that receives a compressed representation of a three-dimensional medical image generated from the three-dimensional medical image by an encoder network of a deep neural network model comprising an encoder network and the decoder network, wherein the deep neural network model is tailored to a segmentation task related to the three-dimensional medical image, and wherein the reception component receives the compressed representation from a server device via a network in response to execution of the encoder network on the three-dimensional medical image at the server device;
an interaction component that receives user input relative to a displayed portion of the three-dimensional medical image indicating an object included in the displayed portion for segmentation; and
a segmentation component that, in response to reception of the user input, applies the user input and the compressed representation as input to the decoder network and generates a segmentation mask for the object.

2. The system of claim 1, wherein the user input comprises applied user mark-up data to the displayed portion of the three-dimensional image, the applied user mark-up data selected from the group consisting of: one or more points inside the object, one or more points outside the object, one or more points or lines indicating a boundary of the object, free-hand lines or shapes on or around the object, guided lines or shapes on or around the object.

3. The system of claim 1, wherein the computer executable components further comprise:
a preview component that renders the segmentation mask as overlay data over the object and the displayed portion of the three-dimensional medical image in response to generation of the segmentation mask by the segmentation component.

4. The system of claim 3, wherein the interaction component further receives additional user input relative to the displayed portion of the three-dimensional medical image indicating the object included in the displayed portion for updated segmentation, wherein in response to reception of the additional user input, the segmentation component applies the additional user input and the compressed representation as new input to the decoder network and generates an updated segmentation mask for the object, and wherein the preview component renders the updated segmentation mask as new overlay data over the object and the displayed portion of the three-dimensional medical image in response to generation of the updated segmentation mask by the segmentation component.

5. The system of claim 1, wherein the decoder network employs predetermined segmentation weights generated based on simulated user input data relative to training three-dimensional medical images including the object, the simulated user input data indicating the object for segmentation as included in the training three-dimensional images.

6. The system of claim 5, wherein the reception component further receives the predetermined segmentation weights from the server device via the network and applies the predetermined segmentation weights to the decoder network prior to application of the user input and the compresses representation as input to the decoder network to generate the segmentation mask by the segmentation component.

7. The system of claim 5, wherein the deep neural network model was trained using the training three-dimensional medical images as annotated with ground truth segmentation information for the object, and wherein the training comprises generating the simulated user input from the ground truth segmentation information.

8. The system of claim 7, wherein the training further comprises training the encoder network to generate compressed representations of the training three-dimensional medical images and training the decoder network to generate segmentation masks for the object based on the simulated user input data using the compressed representations.

9. The system of claim 8, wherein the computer executable components further comprise:
a training component that performs the deep neural network model training for the segmentation task.

10. A method, comprising:
receiving, by a system comprising a processor from a server device via a network, a compressed representation of a three-dimensional medical image generated from the three-dimensional medical image by an encoder network of a deep neural network model comprising an encoder network and a decoder network, wherein the deep neural network model is tailored to a segmentation task related to the three-dimensional medical image, and wherein the receiving is responsive to execution of the encoder network on the three-dimensional medical image at the server device;
receiving, by the system, user input relative to a displayed portion of the three-dimensional medical image indicating an object included in the displayed portion for segmentation; and
generating, by the system in response to receiving the user input, a segmentation mask for the object based on applying, by the system, the user input and the compressed representation as input to the decoder network.

11. The method of claim 10, further comprising, in response to generating the segmentation mask:
rendering, by the system, the segmentation mask as overlay data over the object and the displayed portion of the three-dimensional medical image in real-time.

12. The method of claim 11, further comprising:
receiving, by the system, additional user input relative to the displayed portion of the three-dimensional medical image indicating the object included in the displayed portion for updated segmentation;
generating, by the system in response to receiving the additional user input, an updated segmentation mask for the object based on applying, by the system, the additional user input and the compressed representation as new input to the decoder network; and
rendering, by the system in response to generating the updated segmentation mask, the updated segmentation mask as new overlay data over the object and the displayed portion of the three-dimensional medical image.

13. The method of claim 10, wherein the decoder network employs predetermined segmentation weights generated based on simulated user input data relative to training three-dimensional medical images including the object, the simulated input data indicating the object for segmentation as included in the training three-dimensional image.

14. The method of claim 13, further comprising:
receiving, by the system from the server device, the predetermined segmentation weights in association with receiving the compressed representation; and
employing, by the system, the predetermined segmentation weights for the decoder network.

15. The method of claim 13, wherein the deep neural network model was trained using the training three-dimensional medical images as annotated with ground truth segmentation information for the object, and wherein the training comprises generating the simulated user input data from the ground truth segmentation information, training the encoder network to generate compressed representations of the training three-dimensional medical images, and training the decoder network to generate segmentation masks for the object based on the simulated user input data and the compressed representations.

16. The method of claim 15, further comprising:
performing, by the system, the deep neural network model training for the segmentation task.

17. A non-transitory machine-readable storage medium, comprising executable instructions that, when executed by a processor at a client device, facilitate performance of operations, comprising:

receiving, from a server device via a network, a compressed representation of a three-dimensional medical image generated from the three-dimensional medical image by an encoder network of a deep neural network model comprising an encoder network and a decoder network, wherein the deep neural network model is tailored to a segmentation task related to the three-dimensional medical image, and wherein the receiving is responsive to execution of the encoder network on the three-dimensional medical image at the server device;
receiving user input relative to a displayed portion of the three-dimensional medical image indicating an object included in the displayed portion for segmentation; and
generating, in response to receiving the user input, a segmentation mask for the object based on applying the user input and the compressed representation as input to the decoder network.

18. The non-transitory machine-readable storage medium of claim 17, wherein the operations further comprise:
receiving additional user input relative to the displayed portion of the three-dimensional medical image indicating the object included in the displayed portion for updated segmentation;
generating, in response to receiving the additional user input, an updated segmentation mask for the object based on applying, by the system, the additional user input and the compressed representation as new input to the decoder network; and
rendering, in response to generating the updated segmentation mask, the updated segmentation mask as new overlay data over the object and the displayed portion of the three-dimensional medical image.

19. The non-transitory machine-readable storage medium of claim 17, wherein the decoder network employs predetermined segmentation weights generated based on simulated user input data relative to training three-dimensional medical images including the object, the simulated input data indicating the object for segmentation as included in the training three-dimensional image.

20. The non-transitory machine-readable storage medium of claim 19, wherein the operations further comprise:
receiving, from the server device, the predetermined segmentation weights in association with receiving the compressed representation; and
employing the predetermined segmentation weights for the decoder network.

* * * * *